US012703867B2

(12) United States Patent
Fujii et al.

(10) Patent No.: US 12,703,867 B2
(45) Date of Patent: Aug. 11, 2026

(54) CELL CAPABLE OF ACTIVATING IMMUNE SYSTEM, AND PHARMACEUTICAL COMPOSITION CONTAINING SAID CELL

(71) Applicant: RIKEN, Saitama (JP)

(72) Inventors: Shinichiro Fujii, Saitama (JP); Kanako Shimizu, Saitama (JP)

(73) Assignee: RIKEN, Saitama (JP)

(*) Notice: Subject to any disclaimer, the term of this patent is extended or adjusted under 35 U.S.C. 154(b) by 974 days.

(21) Appl. No.: 17/618,699

(22) PCT Filed: Jun. 12, 2020

(86) PCT No.: PCT/JP2020/023197
§ 371 (c)(1),
(2) Date: Dec. 13, 2021

(87) PCT Pub. No.: WO2020/251014
PCT Pub. Date: Dec. 17, 2020

(65) Prior Publication Data

US 2022/0251574 A1 Aug. 11, 2022

(30) Foreign Application Priority Data

Jun. 14, 2019 (JP) ................................ 2019-110834

(51) Int. Cl.
*C12N 15/62* (2006.01)
*A61K 38/00* (2006.01)
(Continued)

(52) U.S. Cl.
CPC .............. *C12N 15/62* (2013.01); *A61K 40/10* (2025.01); *A61K 40/4202* (2025.01);
(Continued)

(58) Field of Classification Search
CPC ................ C12N 15/62; C12N 2510/00; C12N 2710/20034; C12N 5/10; C12N 7/00;
(Continued)

(56) References Cited

U.S. PATENT DOCUMENTS

2009/0305979 A1 12/2009 Sung et al.
2010/0196417 A1 8/2010 Tartour
(Continued)

FOREIGN PATENT DOCUMENTS

CN 101421306 A 4/2009
CN 103772508 A 5/2014
(Continued)

OTHER PUBLICATIONS

International Search Report dated Aug. 25, 2020 in PT/JP2020/023197.
(Continued)

*Primary Examiner* — Robert B Mondesi
*Assistant Examiner* — Naghmeh Nina Moazzami
(74) *Attorney, Agent, or Firm* — Foley & Lardner LLP

(57) ABSTRACT

The present invention provides a cell activating the immune system and a pharmaceutical composition containing the cell. According to the present invention, there is provided a mammalian cell having at least one protein selected from the group consisting of E6 protein and E7 protein for early genes of human papillomavirus and a fusion protein of E6 protein and E7 protein, and CD1d protein, wherein the mammalian cell is pulsed with a CD1d ligand. According to the present invention, there are also provided a fusion protein having E7 protein, E6 protein and E7 protein in this order, a nucleic acid encoding the protein and a gene expression vector therefor.

5 Claims, 4 Drawing Sheets

Specification includes a Sequence Listing.

(51) Int. Cl.

| | |
|---|---|
| ***A61K 40/10*** | (2025.01) |
| ***A61K 40/42*** | (2025.01) |
| ***A61K 40/46*** | (2025.01) |
| ***A61P 35/04*** | (2006.01) |
| ***C07K 14/005*** | (2006.01) |
| ***C07K 14/705*** | (2006.01) |
| ***C07K 14/74*** | (2006.01) |
| ***C12N 5/10*** | (2006.01) |
| ***C12N 7/00*** | (2006.01) |

(52) U.S. Cl.

CPC .......... *A61K 40/4271* (2025.01); *A61K 40/46* (2025.01); *A61P 35/04* (2018.01); *C07K 14/005* (2013.01); *C07K 14/70539* (2013.01); *C12N 5/10* (2013.01); *C12N 7/00* (2013.01); *A61K 38/00* (2013.01); *A61K 2239/31* (2023.05); *A61K 2239/38* (2023.05); *A61K 2239/55* (2023.05); *A61K 2239/57* (2023.05); *C07K 2319/00* (2013.01); *C12N 2510/00* (2013.01); *C12N 2710/20022* (2013.01); *C12N 2710/20033* (2013.01); *C12N 2710/20071* (2013.01)

(58) Field of Classification Search

CPC ........... C12N 2710/20022; C12N 2710/20033; C12N 2710/20071; A61K 38/00; A61K 40/10; A61K 40/4202; A61K 40/4271; A61K 40/46; A61K 2239/31; A61K 2239/38; A61K 2239/55; A61K 2239/57; A61K 35/00; A61K 2039/57; A61K 2039/585; A61K 31/7088; A61K 39/12; A61K 35/12; A61K 38/16; A61K 48/0008; A61K 48/005; C07K 2319/00; C07K 14/025; C07K 14/005; C07K 14/70539; C07K 2319/40; A61P 15/00; A61P 35/04; A61P 1/00; A61P 31/12; A61P 31/20; A61P 35/00; A61P 37/04; A61P 43/00

See application file for complete search history.

(56) References Cited

U.S. PATENT DOCUMENTS

| | | | | |
|---|---|---|---|---|
| 2010/0233215 | A1 | 9/2010 | Fujii et al. | |
| 2011/0280895 | A1 | 11/2011 | Fujii et al. | |
| 2013/0189302 | A1 | 7/2013 | Fujii et al. | |
| 2014/0179004 | A1 | 6/2014 | Fujii et al. | |
| 2016/0324952 | A1 | 11/2016 | Bian et al. | |
| 2018/0179257 | A1 | 6/2018 | Orlinger et al. | |
| 2018/0195087 | A1 | 7/2018 | Fujii | |
| 2018/0280487 | A1* | 10/2018 | Petit | C07K 14/195 |
| 2019/0151437 | A1 | 5/2019 | Lichty et al. | |

FOREIGN PATENT DOCUMENTS

| | | | |
|---|---|---|---|
| CN | 106554386 | A | 4/2017 |
| CN | 107921117 | A | 4/2018 |
| CN | 108794623 | A | 11/2018 |
| JP | 2009-534027 | A | 9/2009 |
| JP | 2017-507918 | A | 3/2017 |
| JP | 2018-518172 | A | 7/2018 |
| JP | 2019-514988 | A | 6/2019 |
| WO | WO-2007/097370 | A1 | 8/2007 |
| WO | WO-2010/061930 | A1 | 6/2010 |
| WO | WO-2013/018778 | A1 | 2/2013 |
| WO | WO-2016/198531 | A2 | 12/2016 |

OTHER PUBLICATIONS

Shimizu et al., "Tumor Cells Loaded with alpha-Galactosylceramide Induce Innate NKT and NK Cell-Dependent Resistance to Tumor Implantation in Mice," J. Immunol., 2007, 178:2853-2861.

Liu et al., "Recent progress in researches for action mechanism of adjuvants," Chinese Journal of New Drugs, Nov. 3, 2015, 24(20):2324-2329, with English translation.

Office Action and Search Report dated Jul. 27, 2023 in CN 202080042579.1.

Yubo et al., "Research progress of NKT cell subsets and its role in transplantation immunity," Int. J. Lab. Med., Mar. 30, 2016, 37(6):771-773, with English translation.

Bergot et al., "New Approaches to Immunotherapy for HPV Associated Cancers," Cancers, Sep. 2, 2011, 3(4):3461-3495.

Simova et al., "Therapy for minimal residual tumor disease: [beta]-Galactosylceramide inhibits the growth of recurrent HPV16-associated neoplasms after surgery and chemotherapy," International Journal of Cancer, Sep. 8, 2009, 126(12):2997-3004.

Supplementary European Search Report dated Jun. 12, 2023 in EP 20822017.8.

* cited by examiner

A

B

C

D

Control group

Administration group 1

Administration group 2

```
                         SEQUENCE LISTING


<160> NUMBER OF SEQ ID NOS: 28

<210> SEQ ID NO 1
<211> LENGTH: 158
<212> TYPE: PRT
<213> ORGANISM: Human papillomavirus type 16

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155


<210> SEQ ID NO 2
<211> LENGTH: 98
<212> TYPE: PRT
<213> ORGANISM: Human papillomavirus type 16

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95
```

```
Lys Pro

<210> SEQ ID NO 3
<211> LENGTH: 158
<212> TYPE: PRT
<213> ORGANISM: Human papillomavirus type 18

<400> SEQUENCE: 3

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155


<210> SEQ ID NO 4
<211> LENGTH: 105
<212> TYPE: PRT
<213> ORGANISM: Human papillomavirus type 18

<400> SEQUENCE: 4

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105


<210> SEQ ID NO 5
<211> LENGTH: 256
<212> TYPE: PRT
<213> ORGANISM: Artificial Sequence
<220> FEATURE:
<223> OTHER INFORMATION: E6-E7

<400> SEQUENCE: 5
```

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205

His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255


<210> SEQ ID NO 6
<211> LENGTH: 263
<212> TYPE: PRT
<213> ORGANISM: Artificial Sequence
<220> FEATURE:
<223> OTHER INFORMATION: E6-E7

<400> SEQUENCE: 6

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110
```

-continued

```
Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Pro Lys Ala Thr Leu Gln Asp Ile Val Leu His Leu Glu Pro Gln
                165                 170                 175

Asn Glu Ile Pro Val Asp Leu Leu Cys His Glu Gln Leu Ser Asp Ser
            180                 185                 190

Glu Glu Glu Asn Asp Glu Ile Asp Gly Val Asn His Gln His Leu Pro
        195                 200                 205

Ala Arg Arg Ala Glu Pro Gln Arg His Thr Met Leu Cys Met Cys Cys
    210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln
            260


<210> SEQ ID NO 7
<211> LENGTH: 203
<212> TYPE: PRT
<213> ORGANISM: Artificial Sequence
<220> FEATURE:
<223> OTHER INFORMATION: E6-E7

<400> SEQUENCE: 7

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met His Gly Pro Lys Ala Thr Leu Gln Asp Ile Val Leu His
            100                 105                 110

Leu Glu Pro Gln Asn Glu Ile Pro Val Asp Leu Leu Cys His Glu Gln
        115                 120                 125

Leu Ser Asp Ser Glu Glu Glu Asn Asp Glu Ile Asp Gly Val Asn His
    130                 135                 140

Gln His Leu Pro Ala Arg Arg Ala Glu Pro Gln Arg His Thr Met Leu
145                 150                 155                 160

Cys Met Cys Cys Lys Cys Glu Ala Arg Ile Glu Leu Val Val Glu Ser
                165                 170                 175

Ser Ala Asp Asp Leu Arg Ala Phe Gln Gln Leu Phe Leu Asn Thr Leu
            180                 185                 190

Ser Phe Val Cys Pro Trp Cys Ala Ser Gln Gln
        195                 200
```

<210> SEQ ID NO 8
<211> LENGTH: 256
<212> TYPE: PRT
<213> ORGANISM: Artificial Sequence
<220> FEATURE:
<223> OTHER INFORMATION: E6-E7

<400> SEQUENCE: 8

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205

His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255
```

<210> SEQ ID NO 9
<211> LENGTH: 256
<212> TYPE: PRT
<213> ORGANISM: Artificial Sequence
<220> FEATURE:
<223> OTHER INFORMATION: E7-E6

<400> SEQUENCE: 9

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60
```

```
Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met His Gln Lys Arg Thr Ala Met Phe Gln Asp Pro Gln Glu
            100                 105                 110

Arg Pro Arg Lys Leu Pro Gln Leu Cys Thr Glu Leu Gln Thr Thr Ile
        115                 120                 125

His Asp Ile Ile Leu Glu Cys Val Tyr Cys Lys Gln Gln Leu Leu Arg
    130                 135                 140

Arg Glu Val Tyr Asp Phe Ala Phe Arg Asp Leu Cys Ile Val Tyr Arg
145                 150                 155                 160

Asp Gly Asn Pro Tyr Ala Val Cys Asp Lys Cys Leu Lys Phe Tyr Ser
                165                 170                 175

Lys Ile Ser Glu Tyr Arg His Tyr Cys Tyr Ser Leu Tyr Gly Thr Thr
            180                 185                 190

Leu Glu Gln Gln Tyr Asn Lys Pro Leu Cys Asp Leu Leu Ile Arg Cys
        195                 200                 205

Ile Asn Cys Gln Lys Pro Leu Cys Pro Glu Glu Lys Gln Arg His Leu
    210                 215                 220

Asp Lys Lys Gln Arg Phe His Asn Ile Arg Gly Arg Trp Thr Gly Arg
225                 230                 235                 240

Cys Met Ser Cys Cys Arg Ser Ser Arg Thr Arg Arg Glu Thr Gln Leu
                245                 250                 255


<210> SEQ ID NO 10
<211> LENGTH: 263
<212> TYPE: PRT
<213> ORGANISM: Artificial Sequence
<220> FEATURE:
<223> OTHER INFORMATION: E7-E6

<400> SEQUENCE: 10

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met Ala Arg Phe Glu Asp Pro
            100                 105                 110

Thr Arg Arg Pro Tyr Lys Leu Pro Asp Leu Cys Thr Glu Leu Asn Thr
        115                 120                 125

Ser Leu Gln Asp Ile Glu Ile Thr Cys Val Tyr Cys Lys Thr Val Leu
    130                 135                 140

Glu Leu Thr Glu Val Phe Glu Phe Ala Phe Lys Asp Leu Phe Val Val
145                 150                 155                 160

Tyr Arg Asp Ser Ile Pro His Ala Ala Cys His Lys Cys Ile Asp Phe
                165                 170                 175
```

```
Tyr Ser Arg Ile Arg Glu Leu Arg His Tyr Ser Asp Ser Val Tyr Gly
            180                 185                 190

Asp Thr Leu Glu Lys Leu Thr Asn Thr Gly Leu Tyr Asn Leu Leu Ile
        195                 200                 205

Arg Cys Leu Arg Cys Gln Lys Pro Leu Asn Pro Ala Glu Lys Leu Arg
    210                 215                 220

His Leu Asn Glu Lys Arg Arg Phe His Asn Ile Ala Gly His Tyr Arg
225                 230                 235                 240

Gly Gln Cys His Ser Cys Cys Asn Arg Ala Arg Gln Glu Arg Leu Gln
                245                 250                 255

Arg Arg Arg Glu Thr Gln Val
            260


<210> SEQ ID NO 11
<211> LENGTH: 263
<212> TYPE: PRT
<213> ORGANISM: Artificial Sequence
<220> FEATURE:
<223> OTHER INFORMATION: E7-E6

<400> SEQUENCE: 11

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met His Gln Lys Arg Thr Ala
            100                 105                 110

Met Phe Gln Asp Pro Gln Glu Arg Pro Arg Lys Leu Pro Gln Leu Cys
        115                 120                 125

Thr Glu Leu Gln Thr Thr Ile His Asp Ile Ile Leu Glu Cys Val Tyr
    130                 135                 140

Cys Lys Gln Gln Leu Leu Arg Arg Glu Val Tyr Asp Phe Ala Phe Arg
145                 150                 155                 160

Asp Leu Cys Ile Val Tyr Arg Asp Gly Asn Pro Tyr Ala Val Cys Asp
                165                 170                 175

Lys Cys Leu Lys Phe Tyr Ser Lys Ile Ser Glu Tyr Arg His Tyr Cys
            180                 185                 190

Tyr Ser Leu Tyr Gly Thr Thr Leu Glu Gln Gln Tyr Asn Lys Pro Leu
        195                 200                 205

Cys Asp Leu Leu Ile Arg Cys Ile Asn Cys Gln Lys Pro Leu Cys Pro
    210                 215                 220

Glu Glu Lys Gln Arg His Leu Asp Lys Lys Gln Arg Phe His Asn Ile
225                 230                 235                 240

Arg Gly Arg Trp Thr Gly Arg Cys Met Ser Cys Cys Arg Ser Ser Arg
                245                 250                 255

Thr Arg Arg Glu Thr Gln Leu
            260
```

<210> SEQ ID NO 12
<211> LENGTH: 256
<212> TYPE: PRT
<213> ORGANISM: Artificial Sequence
<220> FEATURE:
<223> OTHER INFORMATION: E6-E7-E6

<400> SEQUENCE: 12

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met Ala Arg Phe Glu Asp Pro Thr Arg Arg Pro Tyr Lys Leu
            100                 105                 110

Pro Asp Leu Cys Thr Glu Leu Asn Thr Ser Leu Gln Asp Ile Glu Ile
        115                 120                 125

Thr Cys Val Tyr Cys Lys Thr Val Leu Glu Leu Thr Glu Val Phe Glu
    130                 135                 140

Phe Ala Phe Lys Asp Leu Phe Val Val Tyr Arg Asp Ser Ile Pro His
145                 150                 155                 160

Ala Ala Cys His Lys Cys Ile Asp Phe Tyr Ser Arg Ile Arg Glu Leu
                165                 170                 175

Arg His Tyr Ser Asp Ser Val Tyr Gly Asp Thr Leu Glu Lys Leu Thr
            180                 185                 190

Asn Thr Gly Leu Tyr Asn Leu Leu Ile Arg Cys Leu Arg Cys Gln Lys
        195                 200                 205

Pro Leu Asn Pro Ala Glu Lys Leu Arg His Leu Asn Glu Lys Arg Arg
    210                 215                 220

Phe His Asn Ile Ala Gly His Tyr Arg Gly Gln Cys His Ser Cys Cys
225                 230                 235                 240

Asn Arg Ala Arg Gln Glu Arg Leu Gln Arg Arg Arg Glu Thr Gln Val
                245                 250                 255
```

<210> SEQ ID NO 13
<211> LENGTH: 414
<212> TYPE: PRT
<213> ORGANISM: Artificial Sequence
<220> FEATURE:
<223> OTHER INFORMATION: E6-E7-E6

<400> SEQUENCE: 13

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
```

```
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205

His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255

Met His Gln Lys Arg Thr Ala Met Phe Gln Asp Pro Gln Glu Arg Pro
            260                 265                 270

Arg Lys Leu Pro Gln Leu Cys Thr Glu Leu Gln Thr Thr Ile His Asp
        275                 280                 285

Ile Ile Leu Glu Cys Val Tyr Cys Lys Gln Gln Leu Leu Arg Arg Glu
    290                 295                 300

Val Tyr Asp Phe Ala Phe Arg Asp Leu Cys Ile Val Tyr Arg Asp Gly
305                 310                 315                 320

Asn Pro Tyr Ala Val Cys Asp Lys Cys Leu Lys Phe Tyr Ser Lys Ile
                325                 330                 335

Ser Glu Tyr Arg His Tyr Cys Tyr Ser Leu Tyr Gly Thr Thr Leu Glu
            340                 345                 350

Gln Gln Tyr Asn Lys Pro Leu Cys Asp Leu Leu Ile Arg Cys Ile Asn
        355                 360                 365

Cys Gln Lys Pro Leu Cys Pro Glu Glu Lys Gln Arg His Leu Asp Lys
    370                 375                 380

Lys Gln Arg Phe His Asn Ile Arg Gly Arg Trp Thr Gly Arg Cys Met
385                 390                 395                 400

Ser Cys Cys Arg Ser Ser Arg Thr Arg Arg Glu Thr Gln Leu
                405                 410
```

<210> SEQ ID NO 14
<211> LENGTH: 414
<212> TYPE: PRT
<213> ORGANISM: Artificial Sequence
<220> FEATURE:
<223> OTHER INFORMATION: E6-E7-E6

<400> SEQUENCE: 14

```
Met His Gln Lys Arg Thr Ala Met Phe Gln Asp Pro Gln Glu Arg Pro
```

```
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205

His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255

Met Ala Arg Phe Glu Asp Pro Thr Arg Arg Pro Tyr Lys Leu Pro Asp
            260                 265                 270

Leu Cys Thr Glu Leu Asn Thr Ser Leu Gln Asp Ile Glu Ile Thr Cys
        275                 280                 285

Val Tyr Cys Lys Thr Val Leu Glu Leu Thr Glu Val Phe Glu Phe Ala
    290                 295                 300

Phe Lys Asp Leu Phe Val Val Tyr Arg Asp Ser Ile Pro His Ala Ala
305                 310                 315                 320

Cys His Lys Cys Ile Asp Phe Tyr Ser Arg Ile Arg Glu Leu Arg His
                325                 330                 335

Tyr Ser Asp Ser Val Tyr Gly Asp Thr Leu Glu Lys Leu Thr Asn Thr
            340                 345                 350

Gly Leu Tyr Asn Leu Leu Ile Arg Cys Leu Arg Cys Gln Lys Pro Leu
        355                 360                 365

Asn Pro Ala Glu Lys Leu Arg His Leu Asn Glu Lys Arg Arg Phe His
    370                 375                 380

Asn Ile Ala Gly His Tyr Arg Gly Gln Cys His Ser Cys Cys Asn Arg
385                 390                 395                 400

Ala Arg Gln Glu Arg Leu Gln Arg Arg Arg Glu Thr Gln Val
                405                 410
```

<210> SEQ ID NO 15

```
<211> LENGTH: 421
<212> TYPE: PRT
<213> ORGANISM: Artificial Sequence
<220> FEATURE:
<223> OTHER INFORMATION: E6-E7-E6

<400> SEQUENCE: 15

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Met His
145                 150                 155                 160

Gly Pro Lys Ala Thr Leu Gln Asp Ile Val Leu His Leu Glu Pro Gln
                165                 170                 175

Asn Glu Ile Pro Val Asp Leu Leu Cys His Glu Gln Leu Ser Asp Ser
            180                 185                 190

Glu Glu Glu Asn Asp Glu Ile Asp Gly Val Asn His Gln His Leu Pro
        195                 200                 205

Ala Arg Arg Ala Glu Pro Gln Arg His Thr Met Leu Cys Met Cys Cys
    210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln Met His Gln Lys Arg Thr Ala Met Phe
            260                 265                 270

Gln Asp Pro Gln Glu Arg Pro Arg Lys Leu Pro Gln Leu Cys Thr Glu
        275                 280                 285

Leu Gln Thr Thr Ile His Asp Ile Ile Leu Glu Cys Val Tyr Cys Lys
    290                 295                 300

Gln Gln Leu Leu Arg Arg Glu Val Tyr Asp Phe Ala Phe Arg Asp Leu
305                 310                 315                 320

Cys Ile Val Tyr Arg Asp Gly Asn Pro Tyr Ala Val Cys Asp Lys Cys
                325                 330                 335

Leu Lys Phe Tyr Ser Lys Ile Ser Glu Tyr Arg His Tyr Cys Tyr Ser
            340                 345                 350

Leu Tyr Gly Thr Thr Leu Glu Gln Gln Tyr Asn Lys Pro Leu Cys Asp
        355                 360                 365

Leu Leu Ile Arg Cys Ile Asn Cys Gln Lys Pro Leu Cys Pro Glu Glu
    370                 375                 380
```

```
Lys Gln Arg His Leu Asp Lys Lys Gln Arg Phe His Asn Ile Arg Gly
385                 390                 395                 400

Arg Trp Thr Gly Arg Cys Met Ser Cys Cys Arg Ser Ser Arg Thr Arg
                405                 410                 415

Arg Glu Thr Gln Leu
            420


<210> SEQ ID NO 16
<211> LENGTH: 421
<212> TYPE: PRT
<213> ORGANISM: Artificial Sequence
<220> FEATURE:
<223> OTHER INFORMATION: E6-E7-E6

<400> SEQUENCE: 16

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Met His
145                 150                 155                 160

Gly Pro Lys Ala Thr Leu Gln Asp Ile Val Leu His Leu Glu Pro Gln
                165                 170                 175

Asn Glu Ile Pro Val Asp Leu Leu Cys His Glu Gln Leu Ser Asp Ser
            180                 185                 190

Glu Glu Glu Asn Asp Glu Ile Asp Gly Val Asn His Gln His Leu Pro
        195                 200                 205

Ala Arg Arg Ala Glu Pro Gln Arg His Thr Met Leu Cys Met Cys Cys
    210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln Met Ala Arg Phe Glu Asp Pro Thr Arg
            260                 265                 270

Arg Pro Tyr Lys Leu Pro Asp Leu Cys Thr Glu Leu Asn Thr Ser Leu
        275                 280                 285

Gln Asp Ile Glu Ile Thr Cys Val Tyr Cys Lys Thr Val Leu Glu Leu
    290                 295                 300

Thr Glu Val Phe Glu Phe Ala Phe Lys Asp Leu Phe Val Val Tyr Arg
305                 310                 315                 320
```

```
Asp Ser Ile Pro His Ala Ala Cys His Lys Cys Ile Asp Phe Tyr Ser
                325                 330                 335

Arg Ile Arg Glu Leu Arg His Tyr Ser Asp Ser Val Tyr Gly Asp Thr
            340                 345                 350

Leu Glu Lys Leu Thr Asn Thr Gly Leu Tyr Asn Leu Leu Ile Arg Cys
        355                 360                 365

Leu Arg Cys Gln Lys Pro Leu Asn Pro Ala Glu Lys Leu Arg His Leu
    370                 375                 380

Asn Glu Lys Arg Arg Phe His Asn Ile Ala Gly His Tyr Arg Gly Gln
385                 390                 395                 400

Cys His Ser Cys Cys Asn Arg Ala Arg Gln Glu Arg Leu Gln Arg Arg
                405                 410                 415

Arg Glu Thr Gln Val
            420


<210> SEQ ID NO 17
<211> LENGTH: 414
<212> TYPE: PRT
<213> ORGANISM: Artificial Sequence
<220> FEATURE:
<223> OTHER INFORMATION: E6-E7-E6

<400> SEQUENCE: 17

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205

His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255
```

```
Met His Gln Lys Arg Thr Ala Met Phe Gln Asp Pro Gln Glu Arg Pro
            260                 265                 270

Arg Lys Leu Pro Gln Leu Cys Thr Glu Leu Gln Thr Thr Ile His Asp
        275                 280                 285

Ile Ile Leu Glu Cys Val Tyr Cys Lys Gln Gln Leu Leu Arg Arg Glu
    290                 295                 300

Val Tyr Asp Phe Ala Phe Arg Asp Leu Cys Ile Val Tyr Arg Asp Gly
305                 310                 315                 320

Asn Pro Tyr Ala Val Cys Asp Lys Cys Leu Lys Phe Tyr Ser Lys Ile
                325                 330                 335

Ser Glu Tyr Arg His Tyr Cys Tyr Ser Leu Tyr Gly Thr Thr Leu Glu
            340                 345                 350

Gln Gln Tyr Asn Lys Pro Leu Cys Asp Leu Leu Ile Arg Cys Ile Asn
        355                 360                 365

Cys Gln Lys Pro Leu Cys Pro Glu Glu Lys Gln Arg His Leu Asp Lys
    370                 375                 380

Lys Gln Arg Phe His Asn Ile Arg Gly Arg Trp Thr Gly Arg Cys Met
385                 390                 395                 400

Ser Cys Cys Arg Ser Ser Arg Thr Arg Arg Glu Thr Gln Leu
                405                 410


<210> SEQ ID NO 18
<211> LENGTH: 414
<212> TYPE: PRT
<213> ORGANISM: Artificial Sequence
<220> FEATURE:
<223> OTHER INFORMATION: E6-E7-E6

<400> SEQUENCE: 18

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Asp Thr Pro Thr Leu His Glu Tyr Met Leu Asp Leu Gln Pro Glu
                165                 170                 175

Thr Thr Asp Leu Tyr Cys Tyr Glu Gln Leu Asn Asp Ser Ser Glu Glu
            180                 185                 190

Glu Asp Glu Ile Asp Gly Pro Ala Gly Gln Ala Glu Pro Asp Arg Ala
        195                 200                 205
```

```
His Tyr Asn Ile Val Thr Phe Cys Cys Lys Cys Asp Ser Thr Leu Arg
    210                 215                 220

Leu Cys Val Gln Ser Thr His Val Asp Ile Arg Thr Leu Glu Asp Leu
225                 230                 235                 240

Leu Met Gly Thr Leu Gly Ile Val Cys Pro Ile Cys Ser Gln Lys Pro
                245                 250                 255

Met Ala Arg Phe Glu Asp Pro Thr Arg Arg Pro Tyr Lys Leu Pro Asp
            260                 265                 270

Leu Cys Thr Glu Leu Asn Thr Ser Leu Gln Asp Ile Glu Ile Thr Cys
        275                 280                 285

Val Tyr Cys Lys Thr Val Leu Glu Leu Thr Glu Val Phe Glu Phe Ala
    290                 295                 300

Phe Lys Asp Leu Phe Val Val Tyr Arg Asp Ser Ile Pro His Ala Ala
305                 310                 315                 320

Cys His Lys Cys Ile Asp Phe Tyr Ser Arg Ile Arg Glu Leu Arg His
                325                 330                 335

Tyr Ser Asp Ser Val Tyr Gly Asp Thr Leu Glu Lys Leu Thr Asn Thr
            340                 345                 350

Gly Leu Tyr Asn Leu Leu Ile Arg Cys Leu Arg Cys Gln Lys Pro Leu
        355                 360                 365

Asn Pro Ala Glu Lys Leu Arg His Leu Asn Glu Lys Arg Arg Phe His
    370                 375                 380

Asn Ile Ala Gly His Tyr Arg Gly Gln Cys His Ser Cys Cys Asn Arg
385                 390                 395                 400

Ala Arg Gln Glu Arg Leu Gln Arg Arg Arg Glu Thr Gln Val
                405                 410


<210> SEQ ID NO 19
<211> LENGTH: 421
<212> TYPE: PRT
<213> ORGANISM: Artificial Sequence
<220> FEATURE:
<223> OTHER INFORMATION: E6-E7-E6

<400> SEQUENCE: 19

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160
```

```
Gly Pro Lys Ala Thr Leu Gln Asp Ile Val Leu His Leu Glu Pro Gln
                165                 170                 175

Asn Glu Ile Pro Val Asp Leu Leu Cys His Glu Gln Leu Ser Asp Ser
            180                 185                 190

Glu Glu Glu Asn Asp Glu Ile Asp Gly Val Asn His Gln His Leu Pro
        195                 200                 205

Ala Arg Arg Ala Glu Pro Gln Arg His Thr Met Leu Cys Met Cys Cys
    210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln Met His Gln Lys Arg Thr Ala Met Phe
            260                 265                 270

Gln Asp Pro Gln Glu Arg Pro Arg Lys Leu Pro Gln Leu Cys Thr Glu
        275                 280                 285

Leu Gln Thr Thr Ile His Asp Ile Ile Leu Glu Cys Val Tyr Cys Lys
    290                 295                 300

Gln Gln Leu Leu Arg Arg Glu Val Tyr Asp Phe Ala Phe Arg Asp Leu
305                 310                 315                 320

Cys Ile Val Tyr Arg Asp Gly Asn Pro Tyr Ala Val Cys Asp Lys Cys
                325                 330                 335

Leu Lys Phe Tyr Ser Lys Ile Ser Glu Tyr Arg His Tyr Cys Tyr Ser
            340                 345                 350

Leu Tyr Gly Thr Thr Leu Glu Gln Gln Tyr Asn Lys Pro Leu Cys Asp
        355                 360                 365

Leu Leu Ile Arg Cys Ile Asn Cys Gln Lys Pro Leu Cys Pro Glu Glu
    370                 375                 380

Lys Gln Arg His Leu Asp Lys Lys Gln Arg Phe His Asn Ile Arg Gly
385                 390                 395                 400

Arg Trp Thr Gly Arg Cys Met Ser Cys Cys Arg Ser Ser Arg Thr Arg
                405                 410                 415

Arg Glu Thr Gln Leu
            420
```

<210> SEQ ID NO 20
<211> LENGTH: 421
<212> TYPE: PRT
<213> ORGANISM: Artificial Sequence
<220> FEATURE:
<223> OTHER INFORMATION: E6-E7-E6

<400> SEQUENCE: 20

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95
```

```
Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Pro Lys Ala Thr Leu Gln Asp Ile Val Leu His Leu Glu Pro Gln
                165                 170                 175

Asn Glu Ile Pro Val Asp Leu Leu Cys His Glu Gln Leu Ser Asp Ser
            180                 185                 190

Glu Glu Glu Asn Asp Glu Ile Asp Gly Val Asn His Gln His Leu Pro
        195                 200                 205

Ala Arg Arg Ala Glu Pro Gln Arg His Thr Met Leu Cys Met Cys Cys
    210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln Met Ala Arg Phe Glu Asp Pro Thr Arg
            260                 265                 270

Arg Pro Tyr Lys Leu Pro Asp Leu Cys Thr Glu Leu Asn Thr Ser Leu
        275                 280                 285

Gln Asp Ile Glu Ile Thr Cys Val Tyr Cys Lys Thr Val Leu Glu Leu
    290                 295                 300

Thr Glu Val Phe Glu Phe Ala Phe Lys Asp Leu Phe Val Val Tyr Arg
305                 310                 315                 320

Asp Ser Ile Pro His Ala Ala Cys His Lys Cys Ile Asp Phe Tyr Ser
                325                 330                 335

Arg Ile Arg Glu Leu Arg His Tyr Ser Asp Ser Val Tyr Gly Asp Thr
            340                 345                 350

Leu Glu Lys Leu Thr Asn Thr Gly Leu Tyr Asn Leu Leu Ile Arg Cys
        355                 360                 365

Leu Arg Cys Gln Lys Pro Leu Asn Pro Ala Glu Lys Leu Arg His Leu
    370                 375                 380

Asn Glu Lys Arg Arg Phe His Asn Ile Ala Gly His Tyr Arg Gly Gln
385                 390                 395                 400

Cys His Ser Cys Cys Asn Arg Ala Arg Gln Glu Arg Leu Gln Arg Arg
                405                 410                 415

Arg Glu Thr Gln Val
            420
```

<210> SEQ ID NO 21
<211> LENGTH: 354
<212> TYPE: PRT
<213> ORGANISM: Artificial Sequence
<220> FEATURE:
<223> OTHER INFORMATION: E7-E6-E7

<400> SEQUENCE: 21

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

```
Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met His Gln Lys Arg Thr Ala Met Phe Gln Asp Pro Gln Glu
            100                 105                 110

Arg Pro Arg Lys Leu Pro Gln Leu Cys Thr Glu Leu Gln Thr Thr Ile
        115                 120                 125

His Asp Ile Ile Leu Glu Cys Val Tyr Cys Lys Gln Gln Leu Leu Arg
    130                 135                 140

Arg Glu Val Tyr Asp Phe Ala Phe Arg Asp Leu Cys Ile Val Tyr Arg
145                 150                 155                 160

Asp Gly Asn Pro Tyr Ala Val Cys Asp Lys Cys Leu Lys Phe Tyr Ser
                165                 170                 175

Lys Ile Ser Glu Tyr Arg His Tyr Cys Tyr Ser Leu Tyr Gly Thr Thr
            180                 185                 190

Leu Glu Gln Gln Tyr Asn Lys Pro Leu Cys Asp Leu Leu Ile Arg Cys
        195                 200                 205

Ile Asn Cys Gln Lys Pro Leu Cys Pro Glu Glu Lys Gln Arg His Leu
    210                 215                 220

Asp Lys Lys Gln Arg Phe His Asn Ile Arg Gly Arg Trp Thr Gly Arg
225                 230                 235                 240

Cys Met Ser Cys Cys Arg Ser Ser Arg Thr Arg Arg Glu Thr Gln Leu
                245                 250                 255

Met His Gly Asp Thr Pro Thr Leu His Glu Tyr Met Leu Asp Leu Gln
            260                 265                 270

Pro Glu Thr Thr Asp Leu Tyr Cys Tyr Glu Gln Leu Asn Asp Ser Ser
        275                 280                 285

Glu Glu Glu Asp Glu Ile Asp Gly Pro Ala Gly Gln Ala Glu Pro Asp
    290                 295                 300

Arg Ala His Tyr Asn Ile Val Thr Phe Cys Cys Lys Cys Asp Ser Thr
305                 310                 315                 320

Leu Arg Leu Cys Val Gln Ser Thr His Val Asp Ile Arg Thr Leu Glu
                325                 330                 335

Asp Leu Leu Met Gly Thr Leu Gly Ile Val Cys Pro Ile Cys Ser Gln
            340                 345                 350

Lys Pro
```

<210> SEQ ID NO 22
<211> LENGTH: 361
<212> TYPE: PRT
<213> ORGANISM: Artificial Sequence
<220> FEATURE:
<223> OTHER INFORMATION: E7-E6-E7

<400> SEQUENCE: 22

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

-continued

```
Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met His Gln Lys Arg Thr Ala Met Phe Gln Asp Pro Gln Glu
            100                 105                 110

Arg Pro Arg Lys Leu Pro Gln Leu Cys Thr Glu Leu Gln Thr Thr Ile
        115                 120                 125

His Asp Ile Ile Leu Glu Cys Val Tyr Cys Lys Gln Gln Leu Leu Arg
    130                 135                 140

Arg Glu Val Tyr Asp Phe Ala Phe Arg Asp Leu Cys Ile Val Tyr Arg
145                 150                 155                 160

Asp Gly Asn Pro Tyr Ala Val Cys Asp Lys Cys Leu Lys Phe Tyr Ser
                165                 170                 175

Lys Ile Ser Glu Tyr Arg His Tyr Cys Tyr Ser Leu Tyr Gly Thr Thr
            180                 185                 190

Leu Glu Gln Gln Tyr Asn Lys Pro Leu Cys Asp Leu Leu Ile Arg Cys
        195                 200                 205

Ile Asn Cys Gln Lys Pro Leu Cys Pro Glu Glu Lys Gln Arg His Leu
    210                 215                 220

Asp Lys Lys Gln Arg Phe His Asn Ile Arg Gly Arg Trp Thr Gly Arg
225                 230                 235                 240

Cys Met Ser Cys Cys Arg Ser Ser Arg Thr Arg Arg Glu Thr Gln Leu
                245                 250                 255

Met His Gly Pro Lys Ala Thr Leu Gln Asp Ile Val Leu His Leu Glu
            260                 265                 270

Pro Gln Asn Glu Ile Pro Val Asp Leu Leu Cys His Glu Gln Leu Ser
        275                 280                 285

Asp Ser Glu Glu Glu Asn Asp Glu Ile Asp Gly Val Asn His Gln His
    290                 295                 300

Leu Pro Ala Arg Arg Ala Glu Pro Gln Arg His Thr Met Leu Cys Met
305                 310                 315                 320

Cys Cys Lys Cys Glu Ala Arg Ile Glu Leu Val Val Glu Ser Ser Ala
                325                 330                 335

Asp Asp Leu Arg Ala Phe Gln Gln Leu Phe Leu Asn Thr Leu Ser Phe
            340                 345                 350

Val Cys Pro Trp Cys Ala Ser Gln Gln
        355                 360


<210> SEQ ID NO 23
<211> LENGTH: 354
<212> TYPE: PRT
<213> ORGANISM: Artificial Sequence
<220> FEATURE:
<223> OTHER INFORMATION: E7-E6-E7

<400> SEQUENCE: 23

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

```
Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met Ala Arg Phe Glu Asp Pro Thr Arg Arg Pro Tyr Lys Leu
            100                 105                 110

Pro Asp Leu Cys Thr Glu Leu Asn Thr Ser Leu Gln Asp Ile Glu Ile
        115                 120                 125

Thr Cys Val Tyr Cys Lys Thr Val Leu Glu Leu Thr Glu Val Phe Glu
    130                 135                 140

Phe Ala Phe Lys Asp Leu Phe Val Val Tyr Arg Asp Ser Ile Pro His
145                 150                 155                 160

Ala Ala Cys His Lys Cys Ile Asp Phe Tyr Ser Arg Ile Arg Glu Leu
                165                 170                 175

Arg His Tyr Ser Asp Ser Val Tyr Gly Asp Thr Leu Glu Lys Leu Thr
            180                 185                 190

Asn Thr Gly Leu Tyr Asn Leu Leu Ile Arg Cys Leu Arg Cys Gln Lys
        195                 200                 205

Pro Leu Asn Pro Ala Glu Lys Leu Arg His Leu Asn Glu Lys Arg Arg
    210                 215                 220

Phe His Asn Ile Ala Gly His Tyr Arg Gly Gln Cys His Ser Cys Cys
225                 230                 235                 240

Asn Arg Ala Arg Gln Glu Arg Leu Gln Arg Arg Arg Glu Thr Gln Val
                245                 250                 255

Met His Gly Asp Thr Pro Thr Leu His Glu Tyr Met Leu Asp Leu Gln
            260                 265                 270

Pro Glu Thr Thr Asp Leu Tyr Cys Tyr Glu Gln Leu Asn Asp Ser Ser
        275                 280                 285

Glu Glu Glu Asp Glu Ile Asp Gly Pro Ala Gly Gln Ala Glu Pro Asp
    290                 295                 300

Arg Ala His Tyr Asn Ile Val Thr Phe Cys Cys Lys Cys Asp Ser Thr
305                 310                 315                 320

Leu Arg Leu Cys Val Gln Ser Thr His Val Asp Ile Arg Thr Leu Glu
                325                 330                 335

Asp Leu Leu Met Gly Thr Leu Gly Ile Val Cys Pro Ile Cys Ser Gln
            340                 345                 350

Lys Pro


<210> SEQ ID NO 24
<211> LENGTH: 361
<212> TYPE: PRT
<213> ORGANISM: Artificial Sequence
<220> FEATURE:
<223> OTHER INFORMATION: E-7-E6-E7

<400> SEQUENCE: 24

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
```

```
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Met Ala Arg Phe Glu Asp Pro Thr Arg Arg Pro Tyr Lys Leu
            100                 105                 110

Pro Asp Leu Cys Thr Glu Leu Asn Thr Ser Leu Gln Asp Ile Glu Ile
        115                 120                 125

Thr Cys Val Tyr Cys Lys Thr Val Leu Glu Leu Thr Glu Val Phe Glu
    130                 135                 140

Phe Ala Phe Lys Asp Leu Phe Val Val Tyr Arg Asp Ser Ile Pro His
145                 150                 155                 160

Ala Ala Cys His Lys Cys Ile Asp Phe Tyr Ser Arg Ile Arg Glu Leu
                165                 170                 175

Arg His Tyr Ser Asp Ser Val Tyr Gly Asp Thr Leu Glu Lys Leu Thr
            180                 185                 190

Asn Thr Gly Leu Tyr Asn Leu Leu Ile Arg Cys Leu Arg Cys Gln Lys
        195                 200                 205

Pro Leu Asn Pro Ala Glu Lys Leu Arg His Leu Asn Glu Lys Arg Arg
    210                 215                 220

Phe His Asn Ile Ala Gly His Tyr Arg Gly Gln Cys His Ser Cys Cys
225                 230                 235                 240

Asn Arg Ala Arg Gln Glu Arg Leu Gln Arg Arg Arg Glu Thr Gln Val
                245                 250                 255

Met His Gly Pro Lys Ala Thr Leu Gln Asp Ile Val Leu His Leu Glu
            260                 265                 270

Pro Gln Asn Glu Ile Pro Val Asp Leu Leu Cys His Glu Gln Leu Ser
        275                 280                 285

Asp Ser Glu Glu Glu Asn Asp Glu Ile Asp Gly Val Asn His Gln His
    290                 295                 300

Leu Pro Ala Arg Arg Ala Glu Pro Gln Arg His Thr Met Leu Cys Met
305                 310                 315                 320

Cys Cys Lys Cys Glu Ala Arg Ile Glu Leu Val Val Glu Ser Ser Ala
                325                 330                 335

Asp Asp Leu Arg Ala Phe Gln Gln Leu Phe Leu Asn Thr Leu Ser Phe
            340                 345                 350

Val Cys Pro Trp Cys Ala Ser Gln Gln
        355                 360


<210> SEQ ID NO 25
<211> LENGTH: 361
<212> TYPE: PRT
<213> ORGANISM: Artificial Sequence
<220> FEATURE:
<223> OTHER INFORMATION: E7-E6-E7

<400> SEQUENCE: 25

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
```

-continued

```
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met His Gln Lys Arg Thr Ala
            100                 105                 110

Met Phe Gln Asp Pro Gln Glu Arg Pro Arg Lys Leu Pro Gln Leu Cys
        115                 120                 125

Thr Glu Leu Gln Thr Thr Ile His Asp Ile Ile Leu Glu Cys Val Tyr
    130                 135                 140

Cys Lys Gln Gln Leu Leu Arg Arg Glu Val Tyr Asp Phe Ala Phe Arg
145                 150                 155                 160

Asp Leu Cys Ile Val Tyr Arg Asp Gly Asn Pro Tyr Ala Val Cys Asp
                165                 170                 175

Lys Cys Leu Lys Phe Tyr Ser Lys Ile Ser Glu Tyr Arg His Tyr Cys
            180                 185                 190

Tyr Ser Leu Tyr Gly Thr Thr Leu Glu Gln Gln Tyr Asn Lys Pro Leu
        195                 200                 205

Cys Asp Leu Leu Ile Arg Cys Ile Asn Cys Gln Lys Pro Leu Cys Pro
    210                 215                 220

Glu Glu Lys Gln Arg His Leu Asp Lys Lys Gln Arg Phe His Asn Ile
225                 230                 235                 240

Arg Gly Arg Trp Thr Gly Arg Cys Met Ser Cys Cys Arg Ser Ser Arg
                245                 250                 255

Thr Arg Arg Glu Thr Gln Leu Met His Gly Asp Thr Pro Thr Leu His
            260                 265                 270

Glu Tyr Met Leu Asp Leu Gln Pro Glu Thr Thr Asp Leu Tyr Cys Tyr
        275                 280                 285

Glu Gln Leu Asn Asp Ser Ser Glu Glu Glu Asp Glu Ile Asp Gly Pro
    290                 295                 300

Ala Gly Gln Ala Glu Pro Asp Arg Ala His Tyr Asn Ile Val Thr Phe
305                 310                 315                 320

Cys Cys Lys Cys Asp Ser Thr Leu Arg Leu Cys Val Gln Ser Thr His
                325                 330                 335

Val Asp Ile Arg Thr Leu Glu Asp Leu Leu Met Gly Thr Leu Gly Ile
            340                 345                 350

Val Cys Pro Ile Cys Ser Gln Lys Pro
        355                 360


<210> SEQ ID NO 26
<211> LENGTH: 368
<212> TYPE: PRT
<213> ORGANISM: Artificial Sequence
<220> FEATURE:
<223> OTHER INFORMATION: E7-E6-E7

<400> SEQUENCE: 26

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
```

-continued

```
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met His Gln Lys Arg Thr Ala
            100                 105                 110

Met Phe Gln Asp Pro Gln Glu Arg Pro Arg Lys Leu Pro Gln Leu Cys
        115                 120                 125

Thr Glu Leu Gln Thr Thr Ile His Asp Ile Ile Leu Glu Cys Val Tyr
    130                 135                 140

Cys Lys Gln Gln Leu Leu Arg Arg Glu Val Tyr Asp Phe Ala Phe Arg
145                 150                 155                 160

Asp Leu Cys Ile Val Tyr Arg Asp Gly Asn Pro Tyr Ala Val Cys Asp
                165                 170                 175

Lys Cys Leu Lys Phe Tyr Ser Lys Ile Ser Glu Tyr Arg His Tyr Cys
            180                 185                 190

Tyr Ser Leu Tyr Gly Thr Thr Leu Glu Gln Gln Tyr Asn Lys Pro Leu
        195                 200                 205

Cys Asp Leu Leu Ile Arg Cys Ile Asn Cys Gln Lys Pro Leu Cys Pro
    210                 215                 220

Glu Glu Lys Gln Arg His Leu Asp Lys Lys Gln Arg Phe His Asn Ile
225                 230                 235                 240

Arg Gly Arg Trp Thr Gly Arg Cys Met Ser Cys Cys Arg Ser Ser Arg
                245                 250                 255

Thr Arg Arg Glu Thr Gln Leu Met His Gly Pro Lys Ala Thr Leu Gln
            260                 265                 270

Asp Ile Val Leu His Leu Glu Pro Gln Asn Glu Ile Pro Val Asp Leu
        275                 280                 285

Leu Cys His Glu Gln Leu Ser Asp Ser Glu Glu Glu Asn Asp Glu Ile
    290                 295                 300

Asp Gly Val Asn His Gln His Leu Pro Ala Arg Arg Ala Glu Pro Gln
305                 310                 315                 320

Arg His Thr Met Leu Cys Met Cys Cys Lys Cys Glu Ala Arg Ile Glu
                325                 330                 335

Leu Val Val Glu Ser Ser Ala Asp Asp Leu Arg Ala Phe Gln Gln Leu
            340                 345                 350

Phe Leu Asn Thr Leu Ser Phe Val Cys Pro Trp Cys Ala Ser Gln Gln
        355                 360                 365


<210> SEQ ID NO 27
<211> LENGTH: 361
<212> TYPE: PRT
<213> ORGANISM: Artificial Sequence
<220> FEATURE:
<223> OTHER INFORMATION: E7-E6-E7

<400> SEQUENCE: 27

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
```

```
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met Ala Arg Phe Glu Asp Pro
            100                 105                 110

Thr Arg Arg Pro Tyr Lys Leu Pro Asp Leu Cys Thr Glu Leu Asn Thr
        115                 120                 125

Ser Leu Gln Asp Ile Glu Ile Thr Cys Val Tyr Cys Lys Thr Val Leu
    130                 135                 140

Glu Leu Thr Glu Val Phe Glu Phe Ala Phe Lys Asp Leu Phe Val Val
145                 150                 155                 160

Tyr Arg Asp Ser Ile Pro His Ala Ala Cys His Lys Cys Ile Asp Phe
                165                 170                 175

Tyr Ser Arg Ile Arg Glu Leu Arg His Tyr Ser Asp Ser Val Tyr Gly
            180                 185                 190

Asp Thr Leu Glu Lys Leu Thr Asn Thr Gly Leu Tyr Asn Leu Leu Ile
        195                 200                 205

Arg Cys Leu Arg Cys Gln Lys Pro Leu Asn Pro Ala Glu Lys Leu Arg
    210                 215                 220

His Leu Asn Glu Lys Arg Arg Phe His Asn Ile Ala Gly His Tyr Arg
225                 230                 235                 240

Gly Gln Cys His Ser Cys Cys Asn Arg Ala Arg Gln Glu Arg Leu Gln
                245                 250                 255

Arg Arg Arg Glu Thr Gln Val Met His Gly Asp Thr Pro Thr Leu His
            260                 265                 270

Glu Tyr Met Leu Asp Leu Gln Pro Glu Thr Thr Asp Leu Tyr Cys Tyr
        275                 280                 285

Glu Gln Leu Asn Asp Ser Ser Glu Glu Glu Asp Glu Ile Asp Gly Pro
    290                 295                 300

Ala Gly Gln Ala Glu Pro Asp Arg Ala His Tyr Asn Ile Val Thr Phe
305                 310                 315                 320

Cys Cys Lys Cys Asp Ser Thr Leu Arg Leu Cys Val Gln Ser Thr His
                325                 330                 335

Val Asp Ile Arg Thr Leu Glu Asp Leu Leu Met Gly Thr Leu Gly Ile
            340                 345                 350

Val Cys Pro Ile Cys Ser Gln Lys Pro
        355                 360


<210> SEQ ID NO 28
<211> LENGTH: 368
<212> TYPE: PRT
<213> ORGANISM: Artificial Sequence
<220> FEATURE:
<223> OTHER INFORMATION: E7-E6-E7

<400> SEQUENCE: 28

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
```

-continued

```
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln Met Ala Arg Phe Glu Asp Pro
            100                 105                 110

Thr Arg Arg Pro Tyr Lys Leu Pro Asp Leu Cys Thr Glu Leu Asn Thr
        115                 120                 125

Ser Leu Gln Asp Ile Glu Ile Thr Cys Val Tyr Cys Lys Thr Val Leu
    130                 135                 140

Glu Leu Thr Glu Val Phe Glu Phe Ala Phe Lys Asp Leu Phe Val Val
145                 150                 155                 160

Tyr Arg Asp Ser Ile Pro His Ala Ala Cys His Lys Cys Ile Asp Phe
                165                 170                 175

Tyr Ser Arg Ile Arg Glu Leu Arg His Tyr Ser Asp Ser Val Tyr Gly
            180                 185                 190

Asp Thr Leu Glu Lys Leu Thr Asn Thr Gly Leu Tyr Asn Leu Leu Ile
        195                 200                 205

Arg Cys Leu Arg Cys Gln Lys Pro Leu Asn Pro Ala Glu Lys Leu Arg
    210                 215                 220

His Leu Asn Glu Lys Arg Arg Phe His Asn Ile Ala Gly His Tyr Arg
225                 230                 235                 240

Gly Gln Cys His Ser Cys Cys Asn Arg Ala Arg Gln Glu Arg Leu Gln
                245                 250                 255

Arg Arg Arg Glu Thr Gln Val Met His Gly Pro Lys Ala Thr Leu Gln
            260                 265                 270

Asp Ile Val Leu His Leu Glu Pro Gln Asn Glu Ile Pro Val Asp Leu
        275                 280                 285

Leu Cys His Glu Gln Leu Ser Asp Ser Glu Glu Glu Asn Asp Glu Ile
    290                 295                 300

Asp Gly Val Asn His Gln His Leu Pro Ala Arg Arg Ala Glu Pro Gln
305                 310                 315                 320

Arg His Thr Met Leu Cys Met Cys Cys Lys Cys Glu Ala Arg Ile Glu
                325                 330                 335

Leu Val Val Glu Ser Ser Ala Asp Asp Leu Arg Ala Phe Gln Gln Leu
            340                 345                 350

Phe Leu Asn Thr Leu Ser Phe Val Cys Pro Trp Cys Ala Ser Gln Gln
        355                 360                 365
```

CELL CAPABLE OF ACTIVATING IMMUNE SYSTEM, AND PHARMACEUTICAL COMPOSITION CONTAINING SAID CELL

CROSS-REFERENCE TO RELATED APPLICATIONS

This application is the U.S. National Stage of PCT/JP2020/023197, filed Jun. 12, 2020, which claims priority to JP 2019-110834, filed Jun. 14, 2019.

The instant application contains a Sequence Listing which has been submitted in ASCII format via EFS-WEB and is hereby incorporated by reference in its entirety. Said ASCII copy, created on Dec. 23, 2025, is named sequence.txt and is 77,667 bytes.

TECHNICAL FIELD

The present invention relates to a cell activating the immune system and a pharmaceutical composition containing the cell.

BACKGROUND ART

Human papillomavirus (HPV) is a virus known to cause cervical cancer. Other than cervical cancer, HPV causes exogenous intraepithelial tumor and vaginal intraepithelial neoplasia, which develop into vulvar cancer and vaginal cancer, respectively. Recently HPV is also known to have a risk of developing mesopharyngeal carcinoma. Typical HPVs causing cervical cancer are 16 HPV and 18 HPV, which are responsible for 65% of the causes of cervical cancer. Cervical cancer caused by 16 HPV and 18 HPV develops faster than other high-risk cervical cancers. About 80% to 90% of the cervical cancer of women in their 20's to 30's are caused by 16 HPV and 18 HPV.

A cell obtained by pulsing a cell co-expressing CD1d and a target protein with a CD1d ligand is called an artificial adjuvant vector cell (aAVC), which induces an innate immune response and an acquired immune response to the target protein in subjects administered with aAVC (Patent Literatures 1 to 3 and non-patent literature 1).

CITATION LIST

Patent Literatures

Patent Literature 1: WO2007/097370
Patent Literature 2: WO2010/061930
Patent Literature 3: WO2013/018778

Non Patent Literature

Non Patent Literature 1: Shimizu K. et al., 2007, J. Immunol., Vol. 178, pp 2853-2861

SUMMARY OF INVENTION

The present invention provides a cell activating the immune system and a pharmaceutical composition containing the cell.

According to the present invention, the artificial adjuvant vector cell (aAVC) expressing E6 protein or E7 protein activates NKT cells to induce E6 and E7 antigen specific T cell, thereby exerting an anti-tumor effect. According to the present invention, fusion proteins of E6 protein and E7 protein, in particular, a fusion protein of E7 protein, E6 protein and E7 protein linked in this order, is highly expressed within a cell. The present invention is based on such a finding.

Accordingly, the present invention provides, e.g., the following aspects (e.g., industrially available inventions).

(1) A mammalian cell expressing at least one protein selected from the group consisting of E6 protein and E7 protein for early genes of human papillomavirus and a fusion protein of E6 protein and E7 protein, and expressing CD1d protein, wherein the mammalian cell is pulsed with a CD1d ligand.

(2) The cell according to (1), wherein the E6 protein and E7 protein for early genes of human papillomavirus are independently expressed.

(3) The cell according to (2), wherein the E6 protein and E7 protein for early genes of human papillomavirus are expressed in the form of a fusion protein.

(4) The cell according to (3), wherein the fusion protein comprises E7 protein, E6 protein and E7 protein in this order.

(5) A fusion protein comprising E7 protein, E6 protein and E7 protein in this order.

(6) A nucleic acid encoding a fusion protein comprising E7 protein, E6 protein and E7 protein in this order.

(7) An expression vector for a fusion protein comprising E7 protein, E6 protein and E7 protein in this order, the vector containing a nucleic acid encoding the fusion protein.

(8) A pharmaceutical composition comprising the cell according to any one of (1) to (4), the fusion protein according to (5), the nucleic acid according to (6) or the vector according to (7).

(9) The pharmaceutical composition according to (8), for administration to a human subject infected with human papillomavirus.

(10) The pharmaceutical composition according to (9), wherein the human subject has a cancer caused by human papillomavirus.

(11) The pharmaceutical composition according to (10), wherein the cancer caused by human papillomavirus is a cancer selected from the group consisting of cervical cancer, anal cancer and vaginal cancer.

BRIEF DESCRIPTION OF DRAWINGS

FIG. 4 shows the quantification results of E6 protein expression levels measured by western blotting using an anti-E6 antibody. In the figure, #1: E6 expressing HEK293 cells, #2: E7 expressing HEK293 cell, #3: E6-E7 expressing HEK293 cell, #4:

E6-E7-E6 expressing HEK293 cell, #5: E7-E6-E7 expressing HEK293 cell and #6: E7-E6 expressing HEK293 cell. The expression levels are each indicated by the ratio (ratio to E6 protein expression) to the expression level of #1 (regarded as 1).

Figure 5:
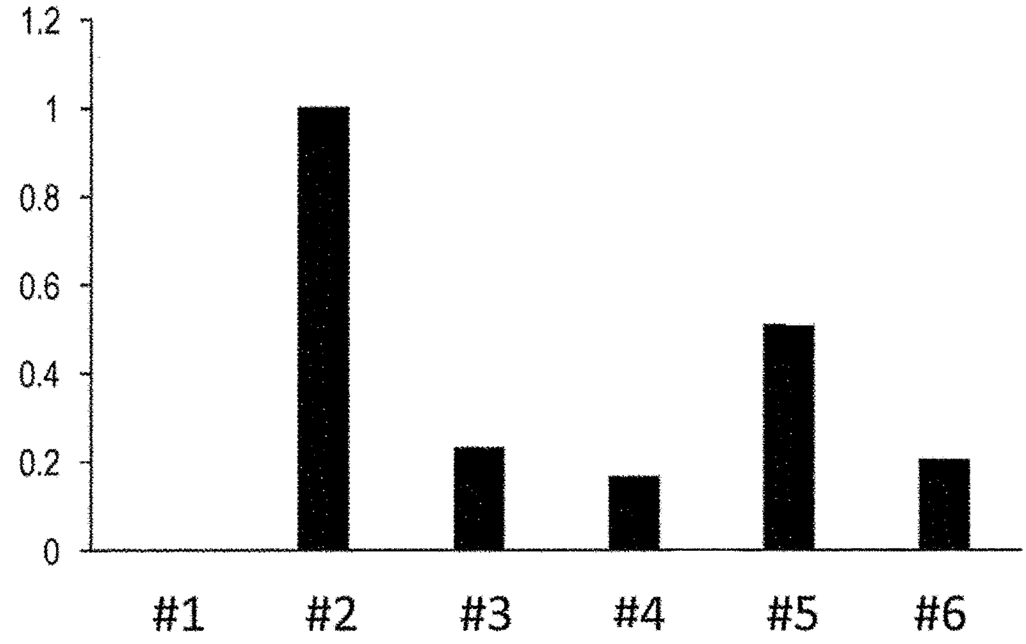

FIG. 5 shows the expression levels of E7 protein in HEK293 cells which were forced to express E6 protein, E7 protein or a fusion protein of these. FIG. 5 shows the quantification results of E7 protein expression levels measured by western blotting using an anti-E7 antibody. In the figure, #1: E6 expressing HEK293 cell, #2: E7 expressing HEK293 cell, #3: E6-E7 expressing HEK293 cell, #4: E6-E7-E6 expressing HEK293 cell, #5: E7-E6-E7 expressing HEK293 cell and #6: E7-E6 expressing HEK293 cell. The expression levels are each indicated by the ratio (ratio to E7 protein expression) to the expression level of #2 (regarded as 1).

Figure 6:
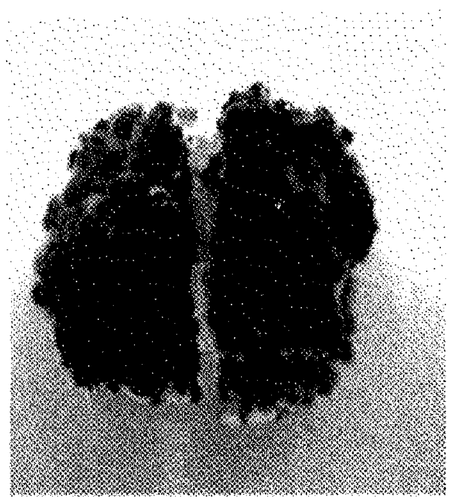
Figure 6:
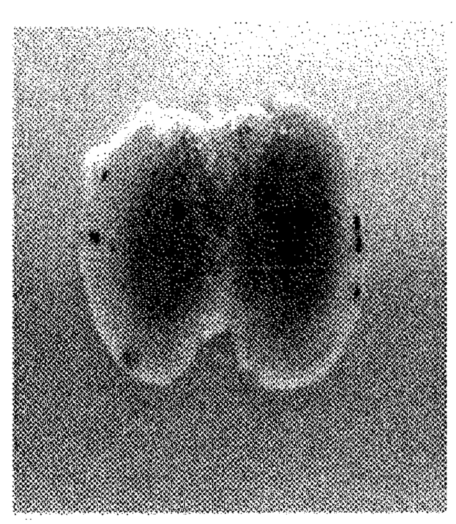

FIG. 6 shows the anti-tumor effect of HEK293 cells expressing CD1d and E7-E6-E7 protein and pulsed with CD1d ligand in melanoma cell transplanted models.

Figure 7:
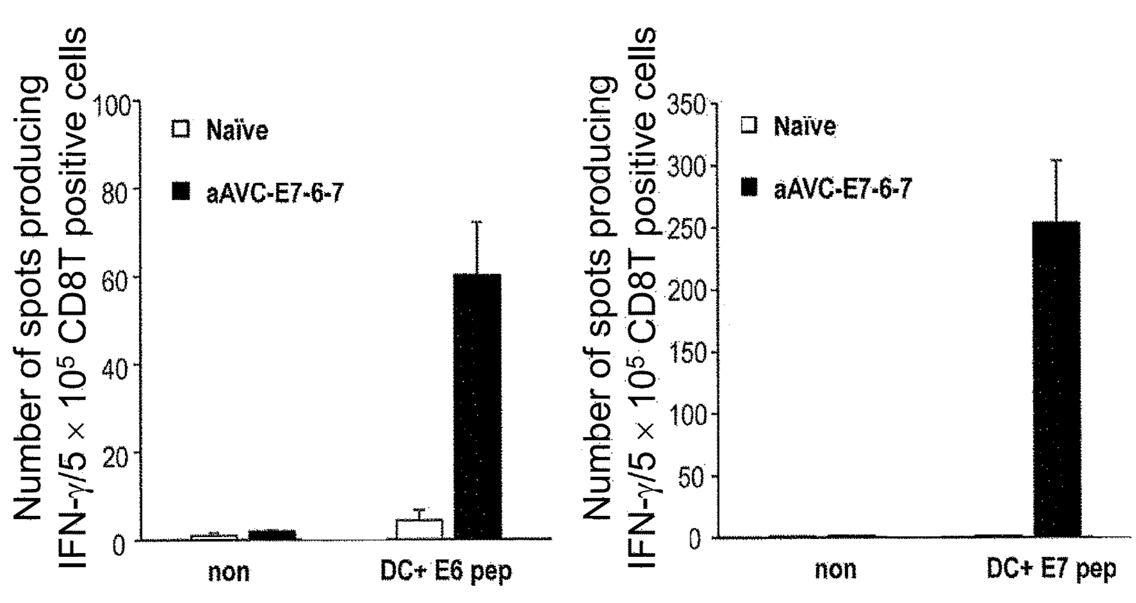

FIG. 7 shows the number of IFN-γ producing cells (number of spots) when HEK293 cells expressing CD1d and E7-E6-E7 protein and pulsed with CD1d ligand were administered and E6 and E7 specific CD8T cells were induced by reimmunization of dendritic cells to which E6 or E7 peptides were added.

DETAILED DESCRIPTION OF THE INVENTION

As used herein, the "subject" may be a mammal including, for example, a human and a non-human mammal. As used herein, the "subject" include a human subject (particularly woman) infected with HPV (for example, HPV-16 and/or HPV-18); a human subject (particularly woman) having a carcinogenic risk increased by infection with HPV and a human subject (particularly woman) who developed cancer by the infection.

As used herein, the "treatment" is meant to include a therapeutic treatment and a preventive treatment. As used herein, the "therapy" is meant to include delaying or stopping the progression of a disease or condition and improving and curing a disease or condition. As used herein, the "prevention" is meant to include suppressing onset of a disease or condition and reducing a rate of incidence.

As used herein, "human papillomavirus" (HPV) refers to a virus belonging to the papillomavirus family and forming warts called as papilloma (or papillary tumor). There are at least 180 genotypes in HPV. Of them, HPV-16 and HPV-18 increase a risk of developing cancer. About 50% of cervical cancers in the world have HPV-16. HPV-16 has E1 to E7 early genes and L1 and L2 late genes. E6 and E7 can be involved in carcinogenesis. Examples of E6 protein include E6 protein of HPV-16 such as E6 protein having an amino acid sequence corresponding to the amino acid sequence registered under GenBank registration number: NP_041325.1 (or the amino acid sequence represented by SEQ ID NO: 1); and E6 protein of HPV-18 such as E6 protein having an amino acid sequence corresponding to the amino acid sequence registered under GenBank registration number: NP_040310.1 or (or the amino acid sequence represented by SEQ ID NO: 2). Examples of E7 protein include E7 protein of HPV-16 such as E7 protein having an amino acid sequence corresponding to the amino acid sequence registered under GenBank registration number: NP_041326.1 (or the amino acid sequence represented by SEQ ID NO: 3); and E7 protein of HPV-18 such as E7 protein having an amino acid sequence corresponding to the amino acid sequence registered under GenBank registration number: NP_040311.1 (or the amino acid sequence represented by SEQ ID NO: 4). As used herein, the "corresponding to an amino acid sequence" refers to an ortholog of the amino acid sequence, in other words, a protein having the same functionality as that of a protein having the amino acid sequence. E6 protein and E7 protein include, for example, E6 proteins and E7 proteins having a sequence identity of 80% or more, 85% or more, 90% or more, 95% or more, 96% or more, 97% or more, 98% or more, and 99% or more, with the respective amino acid sequences mentioned above. The sequence identity refers to a value "Identity" obtained by search based on NEEDLE program (Journal of Molecular Biology, 1970, Vol. 48, p. 443-453) using default parameters, such as Gap penalty=10, Extend penalty=0.5 and Matrix=EBLOSUM62.

As used herein, the "artificial adjuvant vector cell" (aAVC) refers to the cell expressing CD1d and an antigen (for example, E6 protein and E7 protein), wherein the cell was pulsed with CD1d. The cell pulsed with CD1d can be obtained by co-culturing a cell expressing CD1d together with CD1d ligand. The CD1d ligand that fails to attach to cells can be removed by washing. CD1d is a protein of the CD1 family, more specifically, an MHC class I-like glycoprotein. CD1d presents a glycolipid and activates, for example, NKT cells. CD1d include, for example, human CD1d, for example, a protein having the amino acid sequence registered under GenBank registration number: AAH27926.1. The CD1d ligand means a glycolipid binding to CD1d. Examples of the CD1d ligand include, α-GalCer (α-galactosylceramide), α-C-GalCer (α-C-galactosylceramide), iGB3 (isoglobotrihexosylceramide), GD3 (ganglioside 3), GSL-1 (α-bound glucuronic acid) and GSL-1'SA (galacturonic acid), any of which can be used as the CD1d ligand. As the CD1d ligand, for example, α-GalCer and α-C-GalCer can be preferably used.

When aAVC is administered to a mammal, the aAVC activates NKT cells and matures dendritic cells to induce an innate immune response as well as an acquired immune response. If aAVC expresses a protein, acquired immune response to the protein is also induced. An innate immune response and an acquired immune response are induced by aAVC even if any of dendritic cells, cancer cells and other cells (for example, somatic cell) are used. An innate immune response and acquired immune response are induced by aAVC in a subject even if it is isogenic or allogenic aAVC to the subject to be administered. In the case where allogenic aAVC is used, the aAVC itself can be eliminated by the immune system of a subject as a foreign substance after an innate immune response and acquired immune response are induced in the subject. If a target protein is expressed in aAVC, an acquired immune response specific to the target protein can be induced in a subject administered with aAVC. The target protein can be decomposed into partial peptides in aAVC, which can induce an acquired immune response. The aAVC expresses CD1d and pulsed by CD1d ligand. The aAVC may have a foreign gene encoding CD1d operably linked to a regulatory sequence. The aAVC may have a foreign gene encoding a target protein operably linked to a regulatory sequence.

As used herein, the "cell" is a mammalian cell such as a human cell. Examples of the cell include a dendritic cell and a non-dendritic cell. Examples of the cell include a tumor cell and a non-tumor cell. Examples of the cell include a cancer cell and a non-cancer cell. Examples of the cell include an immortalized cell and a primary cell. Examples of the cell include a somatic cell and cells other than the somatic cell. The cell may be isogenic or allogenic to a subject to be administered. Examples of the cell include a human cell and a human cell line, such as a human fetal kidney cell line, for example, HEK293 cell.

As used herein, the "fusion protein" refers to a protein containing two or more proteins or a partial peptide thereof. In the fusion protein, two or more proteins may be linked with or without a spacer interposed between them. The spacer may be a peptide having a length of, for example, 1 to 20 amino acids, 1 to 10 amino acids or 1 to 5 amino acids. A fusion protein obtained by linking protein A and protein B in this order from the N terminal is expressed herein as "protein A-protein B". A fusion protein obtained by linking protein B and protein A in this order from the N terminal is expressed herein as "protein B-protein A". A fusion protein can be designed by linking genes encoding the proteins or partial peptides thereof constituting the protein in frame.

As used herein, the "nucleic acid" refers to deoxyribonucleic acid (DNA) and ribonucleic acid (RNA). Examples of the nucleic acid encoding a protein include DNA and mRNA. DNA may be cDNA having a sequence obtained from mRNA by reverse transcription. In mRNA, the nucleic acid may be modified for ensuring stabilization.

As used herein, the "expression vector" refers to a vector having a regulatory sequence and a nucleic acid encoding a protein and operably linked to the regulatory sequence, and capable of transcribing mRNA encoding the protein in the cell or in vitro. The expression vector may contain, for example, an origin of replication for replicating in a cell, a regulatory sequence, and a nucleic acid encoding a protein and operably linked to the regulatory sequence. The expression vector may have a selective marker (for example, drug resistance gene) for identifying a cell having the vector introduced herein. Examples of the regulatory sequence for expression in mammalian cells include, but are not particularly limited to, a promoter of RNA polymerase II such as CMV immediately early promoter, HSV thymidine kinase promoter, early and late SV40, retrovirus LTR promoter and metallothionein I promoter. Examples of the promoter for expression in *Escherichia coli* include promoters such as lac, trp, lacI, lacZ, T3, T7, gpt, lambda PR, lambda PL and 3-phosphoglycerate kinase. Examples of the promoter for expression in vitro include, but are not particularly limited to, SP6, T7 and T3 promoters. Examples of the expression vector include a plasmid, a phage, a phagemid, a cosmid, a fosmid, an artificial chromosome, a retrovirus, a lentivirus, measles virus, vaccinia virus, adenovirus, adeno-associated virus and Sendai virus.

As used herein, the "cancer" refers to a benign and malignant neoplasm including cancers of stage 0, stage 1, stage 2, stage 3 and stage 4. Examples of the cancer include solid cancers and hematopoietic tumors such as blood cancers (for example, leukemia). Examples of the solid cancer include epithelial cancer and sarcoma. Examples of the cancer include, leukemia, lymphoma (for example, Hodgkin's disease and non-Hodgkin's lymphoma), multiple myeloma, brain tumor, breast cancer, endometrial cancer, cervical cancer, ovarian cancer, vaginal cancer, esophageal cancer, gastric cancer, appendix cancer, colorectal cancer, liver cancer (for example, hepatocellular carcinoma), gallbladder cancer, bile duct cancer, pancreatic cancer, adrenal cancer, gastrointestinal stromal tumor, mesothelioma (for example, pleura, peritoneum and pericardium), head and neck cancer (for example, pharyngeal cancer, oral cancer, gingival cancer, tongue cancer, buccal mucosal cancer), salivary gland cancer, sinus cancer (for example, maxillary sinus cancer, frontal sinus cancer, ethmoid sinus cancer, butterfly bone sinus cancer), thyroid cancer, kidney cancer, lung cancer, osteosarcoma, prostate cancer, testicular cancer, renal cell carcinoma, bladder cancer, rhabdomyosarcoma, skin cancer, anal cancer, neuroblastoma, central nervous system cancer, Wilms tumor, germ cell cancer, soft tissue sarcoma, glioma and glioblastoma. Examples of the cancer caused by human papillomavirus include cervical cancer, anal cancer and vaginal cancer.

According to the present invention, the "target protein" refers to a protein to which an antigen specificity of an acquired immunity is directed, wherein the acquired immunity is induced in a living body. The target protein may be an endogenous protein or an exogenous protein. As used herein, the target protein may be at least one HPV protein selected from the group consisting of E6 protein, E7 protein and a fusion protein of E6 protein and E7 protein. E6 protein and E7 protein may be an HPV protein selected from the group consisting of HPV-16 and HPV-18 proteins. An E6-protein part and an E7-protein part contained in a fusion protein of the present invention may be also an HPV protein selected from the group consisting of HPV-16 and HPV-18 proteins.

As used herein, "express" refers to producing a protein from a nucleic acid encoding the protein in the cell such that the cell has the protein.

According to the present invention, aAVC expressing E6 protein and/or E7 protein serving as an antigen, induces NKT cells and exerts an anti-tumor effect. Accordingly, the present invention provides aAVC expressing E6 protein and/or E7 protein, a pharmaceutical composition containing said aAVC and a pharmaceutical composition containing said aAVC for treating a cancer.

According to the present invention, there is provided a fusion protein of E6 protein and E7 protein. Examples of the fusion protein of E6 protein and E7 protein include a fusion protein selected from the group consisting of E6-E7, E7-E6, E6-E7-E6 and E7-E6-E7 and a protein containing any one of these fusion proteins. According to the present invention, there is provided a nucleic acid (for example, DNA or mRNA) encoding a fusion protein of E6 protein and E7 protein selected from the group consisting of E6-E7, E7-E6, E6-E7-E6 and E7-E6-E7 and proteins containing these fusion proteins. According to the present invention, there is provided an expression vector containing a nucleic acid encoding a fusion protein selected from the group consisting of E6-E7, E7-E6, E6-E7-E6 and E7-E6-E7 and proteins containing these fusion proteins. According to the present invention, there is provided an expression vector for use in said fusion protein in mammalian cells. According to the present invention, there is provided an expression vector for use in expressing said fusion protein in *Escherichia coli*. According to the present invention, there is provided an expression vector for use in transcribing (and preferably translating) a gene encoding said fusion protein in vitro. According to the present invention, there is provided a cell having at least one of the fusion proteins. The cell to be used as aAVC may be a mammalian cell such as a human cell. The cell to be used as aAVC may be a dendritic cell or a non-dendritic cell. The cell may be a tumor cell or a non-tumor cell. The cell to be used as aAVC may be a cancer cell or a non-cancer cell. The cell to be used as aAVC may be immortalized cells or primary cells. The cell to be used as aAVC may be a somatic cell or a cell other than the somatic cell. The cell to be used as aAVC may be isogenic or allogenic to an administration target. The cell to be used as aAVC may be, for example, a human cell line such as a human fetal kidney cell line, for example, HEK293 cell.

The amino acid sequence of an E6-E7 fusion protein is represented by any one of SEQ ID NOs: 5 to 8. The amino acid sequence of an E7-E6 fusion protein is represented by any one of, SEQ ID NOs: 9 to 12. The amino acid sequence of an E6-E7-E6 fusion protein is represented by any one of, SEQ ID NOs: 13 to 20. The amino acid sequence of an E7-E6-E7 fusion protein is represented by any one of, SEQ ID NOs: 21 to 28. These fusion proteins are satisfactory as long as they are expressed within a cell. Even if a fusion protein phagocytosed by a dendritic cell, it is decomposed into small peptides in the dendritic cell. From the small peptides, the immune system to HPV is conceivably induced. Accordingly, a linker may be appropriately introduced into a joining section between proteins in a fusion protein.

According to the present invention, aAVC expressing a E6-E7 fusion protein serving as an antigen incudes NKT cells to produce an anti-tumor effect. Accordingly, the present invention provides aAVC expressing a E6-E7 fusion protein, a pharmaceutical composition containing said aAVC and a pharmaceutical composition containing said aAVC and to be used for treating a cancer.

TABLE 1

| Amino acid sequence from which fusion protein is derived | | | | |
|---|---|---|---|---|
| Fusion protein of proteins A and B or fusion protein of proteins A, B and C | SEQ ID NO: of fusion protein | SEQ ID NO: of amino acids of protein A | SEQ ID NO: of amino acids of protein B | SEQ ID NO: of amino acids of protein C |
| E6-E7 fusion protein | SEQ ID NO: 5 | SEQ ID NO: 1 | SEQ ID NO: 2 | — |
| | SEQ ID NO: 6 | SEQ ID NO: 3 | SEQ ID NO: 4 | — |
| | SEQ ID NO: 7 | SEQ ID NO: 1 | SEQ ID NO: 4 | — |
| | SEQ ID NO: 8 | SEQ ID NO: 3 | SEQ ID NO: 2 | — |
| E7-E6 fusion protein | SEQ ID NO: 9 | SEQ ID NO: 2 | SEQ ID NO: 1 | — |
| | SEQ ID NO: 10 | SEQ ID NO: 4 | SEQ ID NO: 3 | — |
| | SEQ ID NO: 11 | SEQ ID NO: 4 | SEQ ID NO: 1 | — |
| | SEQ ID NO: 12 | SEQ ID NO: 2 | SEQ ID NO: 3 | — |
| E6-E7-E6 fusion protein | SEQ ID NO: 13 | SEQ ID NO: 1 | SEQ ID NO: 2 | SEQ ID NO: 1 |
| | SEQ ID NO: 14 | SEQ ID NO: 1 | SEQ ID NO: 2 | SEQ ID NO: 3 |
| | SEQ ID NO: 15 | SEQ ID NO: 1 | SEQ ID NO: 4 | SEQ ID NO: 1 |
| | SEQ ID NO: 16 | SEQ ID NO: 1 | SEQ ID NO: 4 | SEQ ID NO: 3 |
| | SEQ ID NO: 17 | SEQ ID NO: 3 | SEQ ID NO: 2 | SEQ ID NO: 1 |
| | SEQ ID NO: 18 | SEQ ID NO: 3 | SEQ ID NO: 2 | SEQ ID NO: 3 |
| | SEQ ID NO: 19 | SEQ ID NO: 3 | SEQ ID NO: 4 | SEQ ID NO: 1 |
| | SEQ ID NO: 20 | SEQ ID NO: 3 | SEQ ID NO: 4 | SEQ ID NO: 3 |
| E7-E6-E7 fusion protein | SEQ ID NO: 21 | SEQ ID NO: 2 | SEQ ID NO: 1 | SEQ ID NO: 2 |
| | SEQ ID NO: 22 | SEQ ID NO: 2 | SEQ ID NO: 1 | SEQ ID NO: 4 |
| | SEQ ID NO: 23 | SEQ ID NO: 2 | SEQ ID NO: 3 | SEQ ID NO: 2 |
| | SEQ ID NO: 24 | SEQ ID NO: 2 | SEQ ID NO: 3 | SEQ ID NO: 4 |
| | SEQ ID NO: 25 | SEQ ID NO: 4 | SEQ ID NO: 1 | SEQ ID NO: 2 |

TABLE 1-continued

| Amino acid sequence from which fusion protein is derived | | | | |
|---|---|---|---|---|
| Fusion protein of proteins A and B or fusion protein of proteins A, B and C | SEQ ID NO: of fusion protein | SEQ ID NO: of amino acids of protein A | SEQ ID NO: of amino acids of protein B | SEQ ID NO: of amino acids of protein C |
| | SEQ ID NO: 26 | SEQ ID NO: 4 | SEQ ID NO: 1 | SEQ ID NO: 4 |
| | SEQ ID NO: 27 | SEQ ID NO: 4 | SEQ ID NO: 3 | SEQ ID NO: 2 |
| | SEQ ID NO: 28 | SEQ ID NO: 4 | SEQ ID NO: 3 | SEQ ID NO: 4 |

In Table 1, A-B fusion protein refers to a protein in which A protein and B protein are linked in this order from the N terminal. An example of the amino acid sequence number of the protein is listed in the table. The amino acid sequences in Table 1 may be linked with or without a spacer interposed between them.

According to the present invention, there are provided a fusion protein of the present invention such as an E7-E6-E7 fusion protein or a fusion protein containing E7-E6-E7; a nucleic acid encoding the fusion protein; a gene expression vector containing the nucleic acid; a human cell or human cell line (for example, human fetal kidney cell line, for example, HEK293 cell) expressing the fusion protein; and a human cell or human cell line (for example, human fetal kidney cell line, for example, HEK293 cell) having the nucleic acid (herein, the cells or cell line may further express CD1d). According to the present invention, there are provided a pharmaceutical composition containing a human cell or human cell line expressing a fusion protein of the present invention and a pharmaceutical composition containing a human cell or a human cell line having a nucleic acid encoding a fusion protein of the present invention. According to the present invention further, there are provided a fusion protein of the present invention, for example, an E7-E6-E7 fusion protein or a fusion protein containing E7-E6-E7, a nucleic acid encoding the fusion protein, human aAVC expressing the fusion protein and human aAVC having a nucleic acid encoding the fusion protein. According to the present invention, there is further provided a pharmaceutical composition containing the human aAVC.

E6 protein or E7 protein, or a fusion protein of E6 protein and E7 protein can be expressed in a cell by introducing an expression vector into the cell. E6 protein or E7 protein, or a fusion protein of E6 protein and E7 protein can be expressed in a cell by introduction of mRNA encoding at least one of the proteins into the cell. The expression vector and mRNA can be introduced into a cell by a method known to those skilled in the art. Examples of a method for introducing them include lipofection, electroporation and a calcium phosphate method.

According to the present invention, there is provided a method for producing aAVC expressing E6 protein or E7 protein, or a fusion protein of E6 protein and E7 protein, or producing a pharmaceutical composition containing the aAVC, including introducing mRNA encoding the protein or a fusion protein into a cell. According to the present invention, there is provided a method for producing aAVC expressing an E7-E6-E7 fusion protein or a fusion protein containing E7-E6-E7. According to the present invention, the method for producing aAVC expressing an E7-E6-E7 fusion protein or a fusion protein containing E7-E6-E7, includes introducing mRNA encoding the fusion protein into a cell. The method for producing aAVC of the present invention may include expressing CD1d by a cell and culturing the cell expressing CD1d in the presence of CD1d ligand. The method for producing aAVC of the present invention, if a cell expresses CD1d, may not include artificially expressing CD1d. The method for producing aAVC of the present invention may include culturing a cell expressing CD1d in the presence of CD1d ligand.

According to the present invention, there is provided a method including administering aAVC expressing either one or both of E6 protein and E7 protein of human papillomavirus, to a subject in need. According to the present invention, there is provided a method for treating a cancer in a subject in need, including administering aAVC expressing either one or both of E6 protein and E7 protein of human papillomavirus to the subject in a therapeutically effective amount. According to the present invention, cancer may be a cancer associated with infection with human papillomavirus.

According to the present invention, there is provided a method including administering aAVC expressing an E7-E6-E7 fusion protein or a fusion protein containing E7-E6-E7 to a subject in need. According to the present invention, there is provided a method for treating a cancer in a subject in need, including administering aAVC expressing an E7-E6-E7 fusion protein or a fusion protein containing E7-E6-E7 to the subject in a therapeutically effective amount.

According to the present invention, there is provided use of aAVC expressing either one or both of E6 protein and E7 protein of human papillomavirus in producing a medicament for use in treating a cancer. According to the present invention, there is provided use of aAVC expressing either one or both of E6 protein and E7 protein of human papillomavirus for use in a method for treating a cancer.

According to the present invention, there is provided use of aAVC expressing a fusion protein of the present invention such as an E7-E6-E7 fusion protein or a fusion protein containing E7-E6-E7 in producing a medicament for use in treating a cancer. According to the present invention, aAVC expressing a fusion protein of the present invention such as an E7-E6-E7 fusion protein or a fusion protein containing E7-E6-E7 for use in a method for treating a cancer.

The pharmaceutical composition according to the present invention, may contain aAVC of the present invention and a pharmaceutical acceptable excipient. The pharmaceutical composition according to the present invention can be parenterally (for example, intravenously, intratumorally, intramuscularly, intraperitoneally, intracerebroventricularly and intrathecally) administered. Examples of the pharmaceutically acceptable excipient include a buffer, a tonicity agent, a dispersant, a thickener, a gelling agent, an antioxidant, a preservative and a soothing agent.

According to the present invention, the aAVC of the present invention is expected to produce an antiviral effect in a human subject infected with human papillomavirus. Accordingly, the medical drug or pharmaceutical composition of the present invention can be used for treating a human subject (particularly woman) infected with human papillomavirus, a human subject (particularly woman) having a carcinogenic risk increased by the infection and a human subject (particularly woman) who developed cancer by the infection. The method of the present invention can be a method for treating a human subject (particularly woman) infected with human papillomavirus, a human subject (particularly woman) having a carcinogenic risk increased by the infection and a human subject (particularly woman) who developed cancer by the infection. The medical drug or a pharmaceutical composition of the present invention can be used for treating infection with human papillomavirus in a subject infected with human papillomavirus.

EXAMPLES

Example 1: Preparation of cells expressing viral proteins of human papillomavirus (HPV)

HEK293 strains expressing viral proteins of human papillomavirus (HPV) were prepared and pulsed with α-GalCer.

As the viral proteins of HPV, E6 and E7 proteins encoded respectively by early genes E6 and E7 of HPV16, and fusion proteins of them were designed and put in use. Examples of the fusion proteins designed and put in use include a fusion protein (E6-E7; having the amino acid sequence represented by SEQ ID NO: 5), in which E6 and E7 are linked in this order, a fusion protein (E7-E6; having the amino acid sequence represented by SEQ ID NO: 6), in which E7 and E6 are linked in this order, a fusion protein (E6-E7-E6; having the amino acid sequence represented by SEQ ID NO: 7) in which E6, E7 and E6 are linked in this order, and a fusion protein (E7-E6-E7; having the amino acid sequence represented by SEQ ID NO: 8), in which E7, E6 and E7 are linked in this order.

E6, E7 and designed fusion proteins were separately cloned into a HindIII-EcoRI cleavage site of pGEM4Z-hPV vector (Cat #P2161, company: Promega). In cloning, Kozak sequence (CCACC) was introduced upstream of the initial codon of a gene encoding each of the proteins; a HindIII (restriction enzyme) recognition site was introduced upstream of the Kozak sequence; and an EcoRI (restriction enzyme) recognition site was introduced downstream of a stop codon. In this manner, fusion proteins were integrated into a vector in such a direction that transcription can be made by T7 promoter. The mRNA encoding E6, E7 and the various fusion proteins were prepared by in-vitro transcription system using T7 promoter.

As protein-expressing cell, HEK293 cell or NIH3T3 cell expressing CD1d was used (see, for example, J Immunol. 2007; 178: 2853-2861). Culture was carried out in a culture medium such as AIM-V or 10% FCS containing RPMI1640 at 37° C. under 5% $CO_2$ conditions. Cells were pulsed with CD1d ligand, α-GalCer, by adding α-GalCer (500 ng/mL) to the culture medium followed by culturing. The culture medium was exchanged and mRNA obtained by the in vitro transcription system was introduced into HEK293 cells or NIH3T3 cells by electroporation. Four hours, Eight hours and Sixteen hours after introduction, the cells were collected and expression levels of E6 and E7 proteins were checked by western blotting. The results were as shown in FIG. 1, panels A and B.

Figure 1:
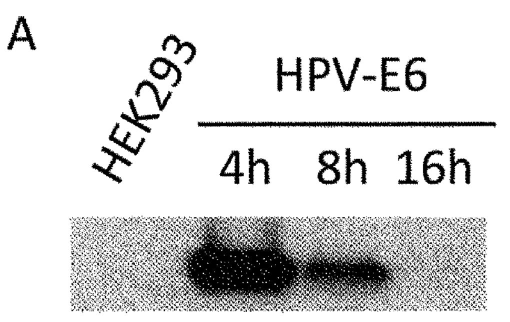
FIG. 1, panels A and B, show expressions of E6 and E7 proteins in cells, which were obtained by pulsing HEK293 cells expressing CD1d with CD1d ligand, and thereafter, transfected with mRNAs encoding E6 and E7 proteins of HPV-16, respectively, and cultured for a predetermined time; and panels C and D show the flow cytometric analysis results of expression of CD1d on the cell surfaces.
Figure 1:
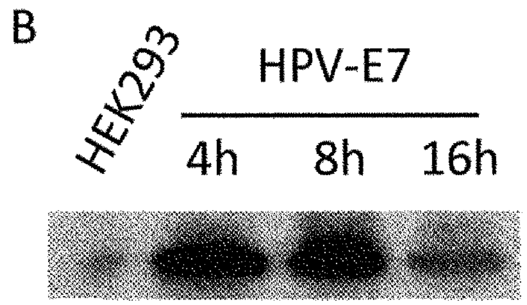
Figure 1:
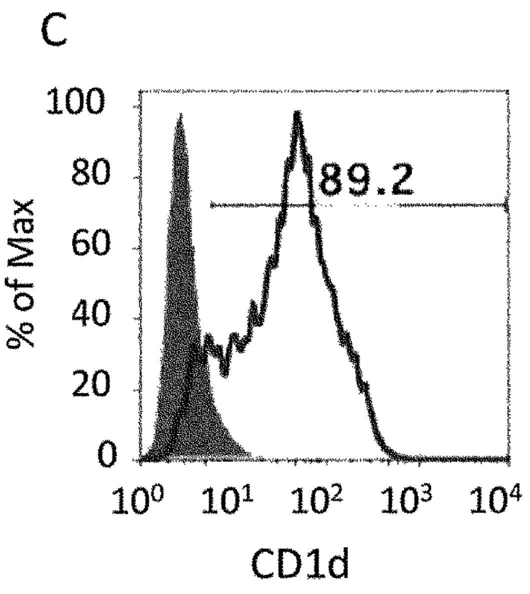
Figure 1:
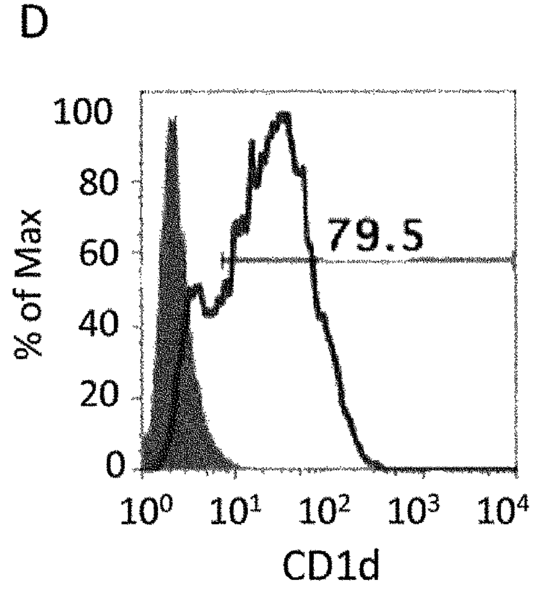

As shown in FIG. 1 (panels A and B), qualitative analysis of E6 protein and E7 protein of HPV in HEK293 cells were made. The expression of CD1d in HEK293 cells was checked by flow cytometry using a PE-conjugated anti-CD1d antibody and FACS Caribur. The results were as shown in FIG. 1, panels C and D. In any one of HEK293 cells, expression of CD1d was confirmed.

Example 2: Immune Response of Cells Expressing CD1d Pulsed with CD1d Ligand, E6 or E7

Figures 2, 3:
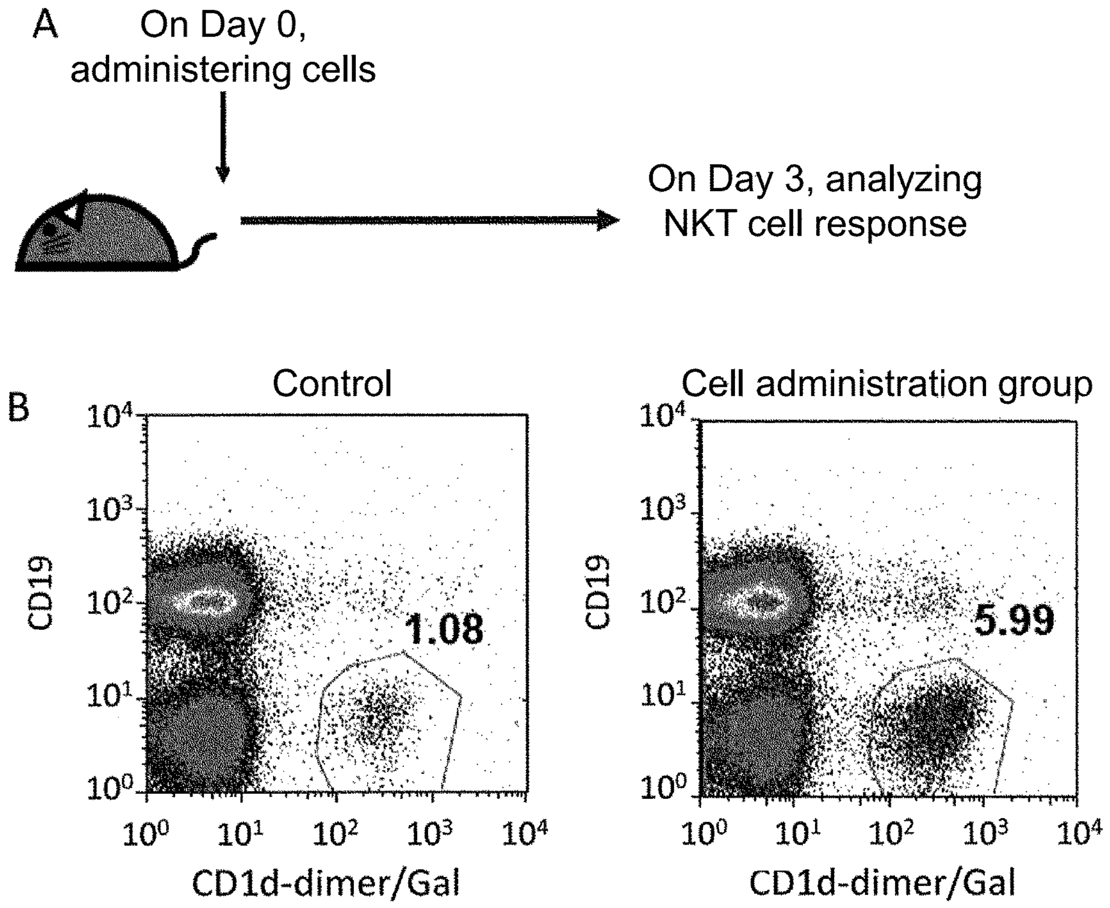
FIG. 2 shows the results of amplification of NKT cell analyzed by the cell, which expresses E6 or E7 protein and is obtained by pulsing HEK293 cell expressing CD1d with CD1d ligand. Panel A shows the experimental scheme. Panel B shows activation of NKT cells.
FIG. 3 shows the anti-tumor effect of a cell, which expresses E6 or E7 protein and is obtained by pulsing NIH3T3 cell expressing CD1d with CD1d ligand, on melanoma transplanted models.

As shown in FIG. 2, panel A, the cells obtained in Example 1 were intravenously administered to mice and in-vivo immune response was checked 3 days later.

To the CD1d-expression cells pulsed with α-GalCer in the same manner as in Example 1, mRNA encoding E6 or E7 was introduced. The cells were collected 4 to 12 hours after introduction. The cells ($5\times10^5$ cells) obtained were intravenously administered to mice (C57BLZ6, 6 to 8 weeks old, female) through the caudal vein. Three days after administration, the spleen was isolated and filtered by a cell strainer. Further, red blood cells were lysed with ACK lysing buffer to prepare spleen cells in 5% FCS containing RPMI. The spleen cells were stained with an anti-CD19 antibody and CD1d-dimer/Gal and analyzed by flow cytometry (results were as shown in FIG. 2, panel B).

As shown in FIG. 2 (panel B), it was found that the number of CD19 negative CD1d-dimer/Gal positive NKT cells increased in the cell administration group. From the results, it was found that the cells administered have an ability to accelerate NKT cells.

Example 3: Examination of Anti-Tumor Effect Using Lung Metastasis Model Animal

In the Example, the cells prepared in Example 2 were transplanted into a lung metastasis model animal and evaluated for anti-tumor effect thereof.

(Preparation and Evaluation of Lung Metastasis Model Animal)

B16 melanoma cells were suspended in PBS so as to have a concentration of $3\times10^5$/200 μl, and intravenously administered to mice (C57BL/6, 6 to 8 weeks old, female) through the caudal vein. To the mice, the cells prepared in Example 2 were administered 3 to 6 hours after administration of melanoma cells. PBS was administered to mice of a control group. To the mice of administration group 1, E6-expressing cells prepared using NIH3T3 cells in accordance with Example 2 were administered. To the mice of administration group 2, E7-expressing cells prepared in Example 2 were administered. Two weeks later, the lung was excised out from the mice, lung metastasis of B16 melanoma cells was observed. The results were as shown in FIG. 3.

As shown in FIG. 3, in the control group, lung metastasis of the melanoma cells was significantly observed. While the entire lung looked black by the presence of melanoma cells in the control group, black color derived from the melanoma cells was virtually not observed in administration group 1 (E6-expressing cell administration group) and administration group 2 (E7-expressing cell administration group). From the results, it was found that E6-expressing cells and E7-expressing cells prepared in Examples both have an anti-tumor effect. From the results of Examples 2 and 3, it was found that CD1d-expressing cells expressing E6 and pulsed with α-GalCer, accelerate NKT cells, in vivo, to activate innate immunity and exert an anti-tumor effect.

Example 4: Preparation of E6-E7 Fusion Protein

In the present invention, a E6-E7 fusion protein was prepared and allowed to express in HEK293 cells. The fusion protein was introduced into cells in the form of mRNA as described in Example 1. Four hours after introduction, the cells were collected. A cell lysate was obtained and analyzed by western blotting to check the expression level of the protein. As the antibody, an anti-E6 antibody was used in the case shown in FIG. 4 and anti-E7 antibody was used in the case shown in FIG. 5. In the same manner as the case shown in FIG. 1, individual proteins were detected by western blotting. The images thereof were imported by a computer and analyzed by image analysis software, Image Reader LAS-1000 pro. With reference of calibration curves prepared based on the densities of bands given by predetermined amounts of E6 protein and E7 protein standard samples, expression levels were obtained based evaluation of the densities of the bands of the samples. The results were as shown in FIGS. 4 and 5, each of which shows the expression ratio relative to the expression level of single-protein-expressing cells (regarded as 1).

Figure 4:
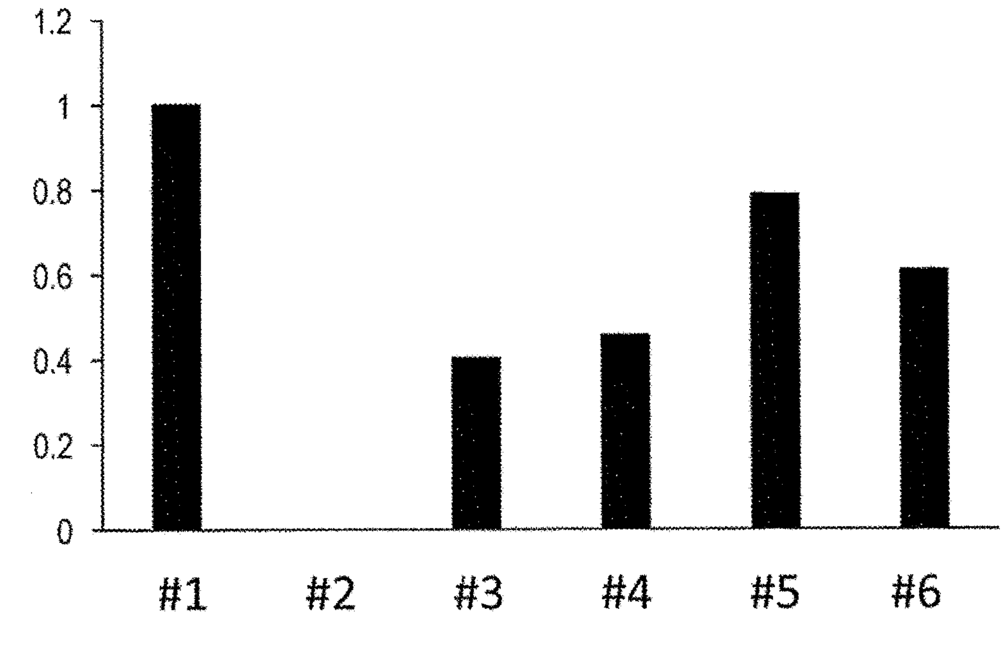
FIG. 4 shows the expression levels of E6 protein in HEK293 cells which were forced to express E6 protein, E7 protein or a fusion protein of these.

In FIGS. 4 and 5, #1 to #6 represent the following cell lysates.

#1: E6 expressing HEK293 cells
#2: E7 expressing HEK293 cells
#3: E6-E7 expressing HEK293 cells
#4: E6-E7-E6 expressing HEK293 cells
#5: E7-E6-E7 expressing HEK293 cells
#6: E7-E6 expressing HEK293 cells As shown in FIG. 4, the E6 expression efficiency of the E6-E7 fusion protein was about half of that of E6 protein, and the E6 expression efficiency of E7-E6-E7 fusion protein was the same as that of the E6 protein.

As shown in FIG. 5, the expression efficiencies of the E6-E7 fusion protein and E6-E7-E6 fusion protein were ⅕ to ¼ times that of E7 protein, whereas the expression efficiency of the E7-E6-E7 fusion protein was more than twice those of the E6-E7 fusion protein and E6-E7-E6 fusion protein.

Example 5: Anti-Tumor Effect of E6-E7 Fusion Protein

To lung metastasis model animals (n=5), which were prepared by transplanting B16 melanoma cells ($3\times10^5$ cells) in the same manner as in Example 3, E7-E6-E7 expressing HEK293 cells ($5\times10^5$ cells) prepared in Example 4 were transplanted and the anti-tumor effect thereof was examined. The results were as shown in FIG. 6. As shown in FIG. 6, the lung metastasis of melanoma cells was obviously observed, the entire lung looked black by the presence of melanoma cells in the control group, black color derived from the melanoma cells was virtually not observed in the E7-E6-E7 administration group. From the results, it was found that E7-E6-E7 expressing cells prepared in Example can activate the innate immune system to produce an anti-tumor effect.

Example 6: Activation of Killer T Cell by aAVC

E7-E6-E7 expressing HEK293 cells ($5\times10^5$ cells; aAVC-E7-6-7) prepared in Example 4 were administered to mice. Seven days later, CD8 single positive T cells ($5\times10^5$ cells) were taken out from the spleen and stimulated with dendritic cells ($1\times10^5$ cells) to which E6 or E7 peptide was added, for 24 hours. At this time, the number of IFN-γ producing CD8T cells (number of spots) were examined by ELISPOT assay. Since the production of IFN-γ is reported to have a correlation with cytotoxic effect (action) of killer T cells, measurement of the cytokine is widely used. The results were as shown in FIG. 7. As shown in FIG. 7, in the E7-E6-E7 administration group, CD8T cells reacted specifically to E6 and E7 to produce IFN-γ were detected. From the results, it was found that aAVC expressing E7-E6-E7 induces E6 and E7 specific killer T cells.

From the above, it is found that E7-E6-E7 fusion protein is suitable for expressing a fusion protein of E6 and E7. It is also found that an E7-E6-E7-expressing cell activates the innate immune system to produce an anti-tumor effect, and, in addition, responses specifically to E6 and E7 to induce a CD8T cell producing IFN-γ. From this, it is believed that the E7-E6-E7-expressing cell activates the innate immune system and simultaneously responses specifically to E6 and E7 to induce a CD8T cell producing IFN-γ, thereby producing an anti-tumor effect. Note that if an E7-E6-E7 fusion protein is expressed in aAVC, it is decomposed into E6 and E7 in a cell to produce small peptides derived from E6 and E7. From this, it is understood that aAVC expressing an E7-E6-E7 fusion protein produces an anti-tumor effect similarly to aAVC expressing E6 and aAVC expressing E7.

SEQUENCE LISTING

[Final] PR13-9014W0 sequence listing.txt

The invention claimed is:

1. A mammalian cell expressing (a) an E7-E6-E7 fusion protein, wherein the fusion protein consists of, from its N-terminus to its C-terminus, a first E7 protein of human papilloma virus (HPV), an E6 protein of HPV, and a second E7 protein of HPV, wherein the E6 protein is flanked by the first E7 protein and the second E7 protein, and wherein (1) each of the first E7 protein and the second E7 protein is an HPV-16 E7 protein, or (2) each of the first E7 protein and the second E7 protein is an HPV-18 E7 protein, and (b) a CD1d protein, wherein the mammalian cell is pulsed with a CD1d ligand, wherein the cell induces antigen-specific T cell immunity against both of E6 and E7 of HPV when an effective amount of the cells is administered to a human subject, and wherein the fusion protein comprises the amino acid sequence set forth in any one of SEQ ID NOs: 21, 23, 26, and 28.

2. A pharmaceutical composition comprising the cell according to claim 1.

3. A method of inducing antigen-specific T cell immunity against both of an E6 protein of human papilloma virus (HPV) and an E7 protein of HPV in a human subject, comprising:

administering to the human subject an effective amount of the cell according to claim 1.

4. A method of treating a human subject infected with human papillomavirus (HPV) comprising:

administering to the human subject an effective amount of the cell according to claim 1.

5. The method of claim 4, wherein the human subject developed cancer by the infection.

* * * * *